US008668986B2

(12) United States Patent
Burckhardt

(10) Patent No.: US 8,668,986 B2
(45) Date of Patent: Mar. 11, 2014

(54) AROMATIC ALDIMINES AND POLYURETHANE COMPOSITIONS WHICH CONTAIN ALDIMINE

(75) Inventor: Urs Burckhardt, Zurich (CH)

(73) Assignee: Sika Technology AG, Baar (CH)

( * ) Notice: Subject to any disclaimer, the term of this patent is extended or adjusted under 35 U.S.C. 154(b) by 456 days.

(21) Appl. No.: 12/742,366

(22) PCT Filed: Nov. 13, 2008

(86) PCT No.: PCT/EP2008/065431
§ 371 (c)(1),
(2), (4) Date: May 11, 2010

(87) PCT Pub. No.: WO2009/062985
PCT Pub. Date: May 22, 2009

(65) Prior Publication Data
US 2010/0255314 A1    Oct. 7, 2010

(30) Foreign Application Priority Data
Nov. 13, 2007    (EP) ..................................... 07120595

(51) Int. Cl.
| | | |
|---|---|---|
| B32B 27/18 | (2006.01) | |
| B32B 27/28 | (2006.01) | |
| B32B 27/38 | (2006.01) | |
| B32B 37/12 | (2006.01) | |
| C07C 67/00 | (2006.01) | |
| C09J 163/00 | (2006.01) | |
| C09J 179/00 | (2006.01) | |

(52) U.S. Cl.
USPC .......... 428/411.1; 428/414; 156/99; 156/330; 156/331.4; 525/408; 525/454; 528/59; 528/407; 560/250

(58) Field of Classification Search
None
See application file for complete search history.

(56) References Cited

U.S. PATENT DOCUMENTS

| 3,881,043 | A | * | 4/1975 | Rieser et al. ..................... 428/81 |
| 4,720,535 | A | * | 1/1988 | Schleier et al. .................. 528/59 |
| 4,853,454 | A | | 8/1989 | Merger et al. |
| 5,955,199 | A | | 9/1999 | Johnson et al. |
| 7,741,425 | B2 | | 6/2010 | Burckhardt et al. |
| 2004/0180155 | A1 | | 9/2004 | Nguyen-Misra et al. |
| 2005/0065276 | A1 | | 3/2005 | Burckhardt et al. |
| 2006/0122352 | A1 | | 6/2006 | Burckhardt |
| 2006/0149025 | A1 | | 7/2006 | Burckhardt |
| 2007/0276058 | A1 | | 11/2007 | Burckhardt et al. |
| 2010/0255314 | A1 | | 10/2010 | Burckhardt |

FOREIGN PATENT DOCUMENTS

| DE | 31 33 769 A1 | 3/1983 |
| EP | 0 832 953 A2 | 4/1998 |
| EP | 1 329 469 A1 | 7/2003 |
| JP | A-06-093242 | 4/1994 |
| WO | WO 2004/013088 A1 | 2/2004 |
| WO | WO 2004/013200 A1 | 2/2004 |
| WO | WO 2007/036575 | 4/2007 |

OTHER PUBLICATIONS

International Preliminary Report on Patentability issued in International Application No. PCT/EP2008/065431 on Jun. 1, 2010 (with English-language translation).
International Search Report issued in International Application No. PCT/EP2008/065431 on Feb. 18, 2009 (with English-language translation).
Jul. 14, 2011 Office Action issued in U.S. Appl. No. 12/312,180.
Feb. 17, 2012 Office Action issued in U.S. Appl. No. 12/312,180.
Oct. 3, 2012 Office Action issued in U.S. Appl. No. 12/312,180.
Apr. 23, 2013 Office Action issued in U.S. Appl. No. 12/312,180.
Aug. 28, 2013 Office Action issued in U.S. Appl. No. 12/312,180.
Müller et al.; "Oxygen Compounds III;" Methods of Organic Chemistry; 1952, pp. 516-529, $4^{th}$ edition. (with English Translation).

* cited by examiner

*Primary Examiner* — Ramsey Zacharia
(74) *Attorney, Agent, or Firm* — Oliff PLC

(57) ABSTRACT

The present invention relates to aromatic aldimines, which are based on primary aromatic polyamines, which are solid at room temperature and liquid at room temperature and which have the lowest possible viscosity, hydrolyze with little odor, and can be used as blocked amines in curable compositions, in particular in compositions having one-component and two-component isocyanate groups. Said compositions have a relatively long open time, but cure surprisingly rapidly, said curing occurring without strong odor formation and without bubbling. In addition, the compositions have outstanding mechanical properties after curing, in particular high strength with high ductility, and good resistance to heat and moisture.

33 Claims, No Drawings

AROMATIC ALDIMINES AND POLYURETHANE COMPOSITIONS WHICH CONTAIN ALDIMINE

TECHNICAL FIELD

The present invention relates to the field of the aldimines and of the moisture-curing polyurethane compositions, and to the use thereof, especially as elastic adhesives, sealants and coatings.

STATE OF THE ART

Aldimines are condensation products of primary amines and aldehydes and constitute a substance class which has been known for some time. On contact with water, aldimines can be hydrolyzed to amines and aldehydes. Owing to this property, they can be used as a protected form of amines, or of aldehydes. For example, aldimines are used in polyurethane chemistry, where they serve as moisture-activable crosslinkers, known as "blocked amines" or "latent hardeners", for one- or two-component compositions comprising isocyanate groups.

Compositions comprising isocyanate groups, also known as polyurethane compositions, are used for a wide variety of different end uses, including as one- and two-component elastic adhesives, sealants or coatings. They have particularly good mechanical strength and thermal stability when they are cured using, at least in part, aromatic polyamines, especially those with primary amino groups. Especially in polyurethane compositions used at room temperature, the use of primary aromatic polyamines as curing agents, however, is complicated by the fact that they are usually relatively high-melting and often sparingly soluble solids. This is true especially of sterically unhindered aromatic polyamines, for example 1,4-phenylenediamine, which has a melting point of more than 140° C. and a low solubility, and is therefore barely useable in free form. Specifically this polyamine would, however, be particularly attractive as a hardener for polyurethane compositions owing to its low amine equivalent weight, the sterically unhindered amino groups in para positions to one another, which impart a high reactivity to it and lead to high mechanical strength, and the comparatively low toxicity thereof for aromatic polyamines. Room temperature liquid primary aromatic polyamines such as 3,5-diethyl-2,4-diaminotoluene or 3,5-dimethylthio-2,4-diaminotoluene generally have sterically hindered amino groups which react relatively slowly, and lead to a significantly lower mechanical strength.

Blocked primary aromatic polyamines in the form of aldimines and the use thereof as curing agents for polyurethane compositions are known, for example, from U.S. Pat. No. 4,720,535 and DE 31 33 769 A1. The aromatic aldimines described there have the disadvantage that they release volatile, odorous aldehydes when they are hydrolyzed and hence in the course of the curing reaction. In addition, like the free polyamines, they are usually solids with a relatively high melting point or are at least highly viscous, and can therefore be used at room temperature only with difficulty.

SUMMARY OF THE INVENTION

It is therefore an object of the present invention to provide aromatic aldimines which are based on room temperature solid primary aromatic polyamines, are liquid at room temperature and have a very low viscosity, are hydrolyzed with low odor and can be used as blocked amines in curable compositions, especially in one- and two-component compositions comprising isocyanate groups.

It has been found that, surprisingly, aromatic dialdimines as claimed in claim 1 achieve this object. By virtue of the reaction of selected room temperature solid primary aromatic diamines with specific ester-containing aldehydes, it is possible to obtain aromatic diamines which hydrolyze with low or zero odor and are surprisingly liquid at room temperature and even usually have a low viscosity. As a result, they can be used in a simple manner as a constituent of curable compositions which are produced and/or used at room temperature. Together with reactive groups, especially together with isocyanate groups, they have a good storage stability.

The invention further provides curable compositions as claimed in claim 11, comprising the aromatic dialdimines described. These compositions comprise, more particularly, at least one polyisocyanate P and have a relatively long open time, but surprisingly cure rapidly in spite of this, which takes place without significant odor formation and without bubble formation. In addition, they possess excellent mechanical properties after the curing, more particularly a high strength coupled with a high extensibility, and good stability to heat and moisture.

Further aspects of the invention are the subject of further independent claims. Particularly preferred embodiments of the invention are the subject of the dependent claims.

Ways of Performing the Invention

The invention provides aromatic dialdimines of the formula (I).

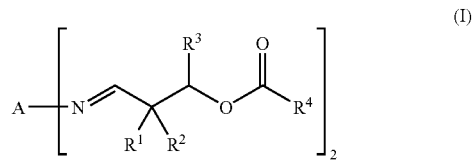

In this formula, A is the radical of a primary aromatic diamine B after the removal of the two primary amino groups, where the diamine B is selected from the group consisting of 1,2-, 1,3- and 1,4-phenylenediamine, 2,4- and 2,6-tolylenediamine (TDA), 3,4-tolylenediamine, 5-isopropyl-2,4-tolylenediamine, 5-(tert-butyl)-2,4-tolylenediamine, 4,6-dialkyl-1,3-phenylenediamines with alkyl groups, which are especially methyl, ethyl, isopropyl or 1-methylpropyl groups, 4,4'-, 2,4'- and 2,2'-diaminodiphenylmethane, 3,3'-dimethyl-4,4'-diaminodiphenylmethane, 3,3'-dichloro-4,4'-diaminodiphenylmethane (MOCA), 3,3'-di-tert-butyl-4,4'-diaminodiphenylmethane, 5,5'-methylenedianthranilic acid, dimethyl 5,5'-methylenedianthranilate, 1,3-propylene bis(4-aminobenzoate), 1,4-butylene bis(4-aminobenzoate) and 1,2-bis(2-aminophenylthio)ethane.

In addition, $R^1$ and $R^2$ are each independently either a monovalent hydrocarbon radical having 1 to 12 carbon atoms, or $R^1$ and $R^2$ together are a divalent hydrocarbon radical which has 4 to 20 carbon atoms and is part of an optionally substituted carbocyclic ring having 5 to 8, preferably 6, carbon atoms.

In addition, $R^3$ is a hydrogen atom or an alkyl group or a cycloalkyl group or an arylalkyl group, especially having 1 to 12 carbon atoms.

In addition, $R^4$ is either a linear or branched alkyl radical having 6 to 20 carbon atoms, optionally having cyclic moieties and optionally having at least one heteroatom, especially in the form of ether, ester or aldehyde oxygen, or $R^4$ is a mono- or polyunsaturated, linear or branched hydrocarbon radical having 6 to 20 carbon atoms.

The dialdimines of the formula (I) are liquid at room temperature.

In the present document, the term "primary amino group" refers to an $NH_2$ group which is bonded to an organic radical, whereas the term "secondary amino group" refers to an NH group which is bonded to two organic radicals which may also together be part of a ring. "Primary diamine" refers to an amine with two primary amino groups.

"Aromatic amino group" refers to an amino group which is bonded to an aromatic or heteroaromatic radical. "Aromatic amine" refers to an organic compound which has exclusively aromatic amino groups.

"Room temperature" refers to a temperature of 23° C.

Preferably, $R^1$ and $R^2$ in formula (I) are each a methyl group.

Additionally preferably, $R^3$ in formula (I) is a hydrogen atom.

Additionally preferably, $R^4$ in formula (I)

is either a linear or branched alkyl radical having 11 to 20 carbon atoms, optionally having cyclic moieties and optionally having at least one heteroatom, especially in the form of ether, ester or aldehyde oxygen, or a mono- or polyunsaturated, linear or branched hydrocarbon radical having 11 to 20 carbon atoms.

More preferably, $R^4$ in formula (I) is an alkyl radical having 11 carbon atoms.

Additionally preferably, A in formula (I) is the radical of a primary aromatic diamine B after the removal of the two primary amino groups, where the diamine B is selected from the group consisting of 1,2-, 1,3- and 1,4-phenylenediamine, 2,4- and 2,6-tolylenediamine, 3,4-tolylenediamine, 4,4'-, 2,4'- and 2,2'-diaminodiphenylmethane and 3,3'-dichloro-4,4'-diaminodiphenylmethane.

Particularly preferred diamines B are 1,3-phenylenediamine, 1,4-phenylenediamine, 2,4-tolylenediamine and 4,4'-diaminodiphenylmethane.

The most preferred diamine B is 1,4-phenylenediamine.

Preferred dialdimines of the formula (I) are 1,3- and 1,4-bis((2,2-dimethyl-3-lauroyloxypropylidene)amino)benzene, 2,4-bis((2,2-dimethyl-3-lauroyloxypropylidene)amino)toluene or 4,4'-bis((2,2-dimethyl-3-lauroyloxypropylidene)amino)diphenylmethane.

A particularly preferred dialdimine of the formula (I) is 1,4-bis((2,2-dimethyl-3-lauroyloxypropylidene)amino)benzene.

An aromatic dialdimine of the formula (I) is obtainable by a condensation reaction with elimination of water between at least one room temperature solid, primary aromatic diamine B of the formula (II) and at least one room temperature liquid aldehyde ALD of the formula (III). The aldehyde ALD of the formula (III) is used here stoichiometrically or in a stoichiometric excess in relation to the amino groups of the diamine. In a preferred process, the diamine B is reacted with the aldehyde ALD of the formula (III) without the use of solvents, and the water formed is removed from the reaction mixture by means of reduced pressure.

$$A\text{---}[NH_2]_2 \quad (II)$$

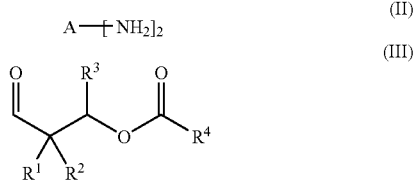
(III)

In the formulae (II) and (III), A, $R^1$, $R^2$, $R^3$ and $R^4$ each have the definitions already mentioned.

The aldehyde ALD of the formula (III) which can be used to prepare an aromatic dialdimine of the formula (I) is liquid at room temperature and is a tertiary aliphatic or tertiary cycloaliphatic aldehyde. The aldehyde ALD of the formula (III) is an ester, which is obtainable especially from the reaction of 2,2-disubstituted 3-hydroxyaldehydes with suitable carboxylic acids.

Carboxylic acids suitable for this reaction are, for example, saturated aliphatic carboxylic acids, such as 2-ethylcaproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachic acid; monounsaturated aliphatic carboxylic acids such as palmitoleic acid, oleic acid; polyunsaturated aliphatic carboxylic acids such as linoleic acid, linolenic acid, eleostearic acid, arachidonic acid, cycloaliphatic carboxylic acids such as cyclohexanecarboxylic acid; fatty acid mixtures from the industrial hydrolysis of natural oils and fats, for example rapeseed oil, sunflower oil, linseed oil, olive oil, coconut oil, oil palm kernel oil and oil palm oil; and monoalkyl and monoaryl dicarboxylates, as obtained from the monoesterification of dicarboxylic acids such as succinic acid, glutaric acid, adipic acid, pimelic acid, suberic acid, azelaic acid, sebacic acid, 1,12-dodecanedioic acid, maleic acid, fumaric acid, hexahydrophthalic acid, hexahydroisophthalic acid, hexahydroterephthalic acid, 3,6,9-trioxa-undecanedioic acid and similar derivatives of polyethylene glycol, with alcohols such as methanol, ethanol, propanol, butanol, higher homologs and isomers of these alcohols.

2,2-Disubstituted 3-hydroxyaldehydes suitable for this reaction are, for example, 2,2-dimethyl-3-hydroxypropanal, 2-hydroxymethyl-2-methylbutanal, 2-hydroxymethyl-2-ethylbutanal, 2-hydroxymethyl-2-methylpentanal, 2-hydroxymethyl-2-ethylhexanal, 1-hydroxymethylcyclopentanecarboxaldehyde, 1-hydroxymethylcyclohexanecarboxaldehyde, 1-hydroxymethylcyclohex-3-enecarboxaldehyde, 2-hydroxymethyl-2-methyl-3-phenylpropanal, 3-hydroxy-2-methyl-2-phenylpropanal and 3-hydroxy-2,2-diphenylpropanal.

Such 2,2-disubstituted 3-hydroxyaldehydes are in turn obtainable from aldol reactions, especially crossed aldol reactions, between primary or secondary aliphatic aldehydes, especially formaldehyde, and secondary aliphatic, secondary arylaliphatic or secondary cycloaliphatic aldehydes, for example isobutyraldehyde, 2-methylbutyraldehyde, 2-ethylbutyraldehyde, 2-methylvaleraldehyde, 2-ethylcapronaldehyde, cyclopentanecarboxaldehyde, cyclohexanecarboxaldehyde, 1,2,3,6-tetrahydrobenzaldehyde, 2-methyl-3-phenylpropionaldehyde, 2-phenylpropionaldehyde (hydratropaldehyde) or diphenylacetaldehyde.

Preferred aldehydes ALD of the formula (III) are 3-cyclohexanoyloxy-2,2-dimethylpropanal, 2,2-dimethyl-3-(2-ethylhexyloxy)propanal, 2,2-dimethyl-3-lauroyloxypropanal, 2,2-dimethyl-3-myristoyloxypropanal, 2,2-dimethyl-3-palmitoyloxypropanal, 2,2-dimethyl-3-stearoyloxypropanal and analogous esters of other 2,2-disubstituted 3-hydroxyaldehydes.

A particularly preferred aldehyde ALD of the formula (III) is 2,2-dimethyl-3-lauroyloxypropanal.

In a preferred method for preparing an aldehyde ALD of the formula (III), a 2,2-disubstituted 3-hydroxyaldehyde, for example 2,2-dimethyl-3-hydroxypropanal, which can be prepared, for example, from formaldehyde (or paraformaldehyde) and isobutyraldehyde, optionally in situ, is reacted with a carboxylic acid to give the corresponding ester. This esterification can be effected without the use of solvents by known methods. These are described, for example, in Houben-Weyl, "Methoden der organischen Chemie" [Methods of Organic Chemistry], Vol. VIII, pages 516-528.

The aldehyde ALD of the formula (III) is low-odor or odorless.

In a preferred embodiment, the aldehyde ALD of the formula (III) is odorless. Odorless aldehydes ALD of the formula (III) are aldehydes ALD1 of the formula (III a)

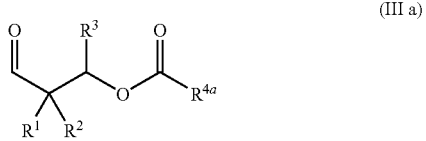

(III a)

where $R^{4a}$ is either a linear or branched alkyl radical having 11 to 20 carbon atoms, optionally having cyclic moieties and optionally having at least one heteroatom, especially oxygen in the form of ether, ester or aldehyde groups, or is a mono- or polyunsaturated, linear or branched hydrocarbon radical having 11 to 20 carbon atoms, and $R^1$, $R^2$ and $R^3$ are each as already defined.

These preferred aldehydes ALD1 of the formula (III a) are odorless and are liquid at room temperature.

Examples of such odorless aldehydes ALD1 are esterification products of the 2,2-disubstituted 3-hydroxyaldehydes already mentioned with carboxylic acids, for example lauric acid, tridecanoic acid, myristic acid, pentadecanoic acid, palmitic acid, margaric acid, stearic acid, nonadecanoic acid, arachic acid, palmitoleic acid, oleic acid, linoleic acid, linolenic acid, elaeostearic acid, arachidonic acid, fatty acids from the industrial hydrolysis of natural oils and fats, for example rapeseed oil, sunflower oil, linseed oil, olive oil, coconut oil, oil palm kernel oil and oil palm oil, and industrial mixtures of fatty acids which comprise these acids. Preferred odorless aldehydes of the formula (III a) are 2,2-dimethyl-3-lauroyloxypropanal, 2,2-dimethyl-3-myristoyloxypropanal, 2,2-dimethyl-3-palmitoyloxypropanal and 2,2-dimethyl-3-stearoyloxypropanal. Particular preference is given to 2,2-dimethyl-3-lauroyloxypropanal.

The dialdimines of the formula (I) have the property that they do not react to a significant degree with isocyanates in the absence of water. The A, $R^1$, $R^2$, $R^3$ and $R^4$ radicals thereof have no moieties which react to a significant degree with isocyanate groups. More particularly, A, $R^1$, $R^2$, $R^3$ and $R^4$ have no hydroxyl groups, no primary or secondary amino groups and no mercapto groups.

The dialdimines of the formula (I) contain sterically hindered aldimino groups which have no hydrogen atom on the α-carbon atom and therefore cannot tautomerize to enamino groups. Owing to this property, they form, together with isocyanate groups, particularly storable, i.e. substantially viscosity-stable, mixtures.

The dialdimines of the formula (I) are surprisingly room temperature liquid substances, even though they are derived from the diamines B mentioned, which are solid at room temperature. For many applications, a liquid state at room temperature is a great advantage, since such substances are useable in compositions without preceding dissolution or melting, more particularly for applications in compositions which are produced and/or applied at room temperature or only slightly elevated temperatures, and which themselves have a liquid or pasty state. Especially surprising is the fact that even dialdimines of the formula (I) which are derived from diamines B with a poor solubility and with a high melting point, for example 1,4-phenylenediamine with a melting point of more than 140° C., are room temperature liquid compounds. Preferred dialdimines of the formula (I) are low-viscosity liquids and have, at 20° C., a viscosity of at most 1000 mPa·s, especially a viscosity between 5 and 500 mPa·s. The term "viscosity" refers in the present document to the dynamic viscosity or shear viscosity, which is defined by the ratio between the shear stress and the shear rate and is determined as described in DIN EN ISO 3219. A low viscosity is an additional advantage for many applications of the dialdimines of the formula (I), especially for applications in compositions which themselves should not have too high a viscosity.

The dialdimines of the formula (I) are additionally low-odor or odorless substances. Preference is given to odorless dialdimines of the formula (I), which are prepared proceeding from the preferred odorless aldehydes ALD1 of the formula (III a). For many applications, odorlessness is a great advantage or an indispensible prerequisite, especially in closed spaces such as in the interior of buildings or vehicles, and in the case of large-area applications, for example in the case of application of floor coverings.

The dialdimines of the formula (I) are storage-stable under suitable conditions. On ingress of moisture, the aldimino groups thereof can be hydrolyzed via intermediates in a formal sense to amino groups, which releases the corresponding aldehydes ALD of the formula (III) which have been used to prepare the dialdimines and are, as already described, low-odor or odorless. Since this hydrolysis reaction is reversible and the chemical equilibrium is clearly on the aldimine side, it can be assumed that, in the absence of compounds reactive toward amines, only some of the aldimino groups are partly or completely hydrolyzed.

The dialdimines of the formula (I) are preparable in a relatively simple process from readily obtainable starting substances. Even though the diamines B used in the preparation thereof are solid at room temperature, the corresponding dialdimines of the formula (I), as already mentioned, are room temperature liquid compounds.

The dialdimines of the formula (I) can be used very widely. They can be used, for example, wherever they can serve as a source of aldehydes ALD of the formula (III) or of diamines B of the formula (II). More particularly, they can be used in aldehyde- and/or amine-reactive systems in the function of protected amines, or protected aldehydes, and be deprotected there in a controlled manner if required. More particularly, they find use in systems in which compounds which react with primary amines are present. The deprotection is effected hydrolytically, for example by contact with water or moisture, especially air humidity.

The dialdimines of the formula (I) are particularly suitable as a constituent of compositions based on at least one isocyanate and/or at least one epoxy resin, especially for applications such as adhesives, sealants, potting compositions, coatings, floor coverings, paints, lacquers, primers or foams, especially when these compositions are to have a low viscosity at room temperature. The use of the room temperature liquid dialdimines of the formula (I) makes it possible to obtain compositions which cure in a formal sense via primary aromatic diamines, especially primary aromatic diamines which have little or no steric hindrance and which, as such, are relatively high-melting and often sparingly soluble solids. By virtue of the use of such diamines in the form of dialdimines of the formula (I) obtainable therefrom, the high melting point and/or the sparing solubility of the dialdimines, even at room temperature, no longer constitutes a difficulty. In the form of its dialdimine of the formula (I), it is more particularly also possible to use the particularly high-melting and sparingly soluble 1,4-phenylenediamine in a simple manner.

The dialdimines of the formula (I) are especially suitable as curing agents for one- or two-component compositions comprising isocyanate groups, such as adhesives, sealants, potting compositions, coatings, floor coverings, paints, lacquers, primers or foams.

Compositions composed of compounds having isocyanate groups and dialdimines of the formula (I) react on contact with water or moisture with hydrolysis of the aldimino groups to give compounds having urea groups. The isocyanate groups react with the primary amino groups which are formally released by the hydrolysis of the aldimino groups to release an aldehyde ALD. Excess isocyanate groups in relation to the aldimino groups react directly with moisture and likewise form urea groups. In the case of suitable stoichiometry between isocyanate groups and aldimino groups, the composition is cured as a result of these reactions; this process is also referred to as crosslinking. The reaction of the isocyanate groups with the aldimino groups being hydrolyzed need not necessarily proceed via free amino groups. It will be appreciated that reactions with intermediates of the hydrolysis reaction are also possible. For example, it is conceivable that an aldimino group being hydrolyzed, in the form of a hemiaminal, reacts directly with an isocyanate group.

Dialdimines of the formula (I) which are prepared proceeding from 1,4-phenylenediamine, the most preferred diamine B, are very particularly suitable as a constituent of compositions comprising isocyanate groups. Dialdimines of the formula (I) derived from 1,4-phenylenediamine are liquids of surprisingly low viscosity at room temperature with good controllability of reactivity toward isocyanate groups, whereas 1,4-phenylenediamine itself has a melting point of more than 140° C., a low solubility and simultaneously a high reactivity toward isocyanate groups, which is difficult to control, and is therefore barely suitable as a curing agent for compositions comprising isocyanate groups.

It is also possible to store the dialdimines of the formula (I) together with water, provided that the dialdimines are stored separately from isocyanate groups. In the course of this, no amines precipitate out in solid form. Only when the water-aldimine mixture comes into contact with isocyanate groups does the hydrolysis proceed to completion. This is because the reaction between dialdimines of the formula (I) and isocyanate groups is also greatly retarded compared to the reaction of the corresponding primary amines when the aldimines are stored together with water.

The invention further provides a curable composition which comprises at least one polyisocyanate P and at least one aromatic dialdimine of the formula (I).

In the present document, the term "polyisocyanate" comprises compounds having two or more isocyanate groups, irrespective of whether they are monomeric polyisocyanates, oligomeric polyisocyanates or polymers which have isocyanate groups and are of relatively high molecular weight.

In one embodiment, a suitable polyisocyanate P is a polyurethane polymer PUP having isocyanate groups.

In the present document, the term "polymer" firstly embraces a collective of macromolecules which are chemically homogeneous but differ in relation to degree of polymerization, molar mass and chain length, which has been prepared by a poly reaction (polymerization, polyaddition, polycondensation). The term secondly also embraces derivatives of such a collective of macromolecules from poly reactions, i.e. compounds which have been obtained by reactions, for example additions or substitutions, of functional groups on given macromolecules, and which may be chemically homogeneous or chemically inhomogeneous. The term further also embraces what are known as prepolymers, i.e. reactive oligomeric preliminary adducts whose functional groups are involved in the formation of macromolecules.

The term "polyurethane polymer" embraces all polymers prepared by what is known as the diisocyanate polyaddition process. This also includes those polymers which are virtually or entirely free of urethane groups. Examples of polyurethane polymers are polyetherpolyurethanes, polyesterpolyurethanes, polyetherpolyureas, polyureas, polyesterpolyureas, polyisocyanurates and polycarbodiimides.

A suitable polyurethane polymer PUP is especially obtainable from the reaction of at least one polyol with at least one polyisocyanate. This reaction can be effected by reacting the polyol and the polyisocyanate by customary methods, for example at temperatures of 50° C. to 100° C., optionally with additional use of suitable catalysts, the polyisocyanate being metered in in such a way that its isocyanate groups are present in a stoichiometric excess in relation to the hydroxyl groups of the polyol. The polyisocyanate is advantageously metered in so as to observe an NCO/OH ratio of 1.3 to 5, especially one of 1.5 to 3. The NCO/OH ratio is understood here to mean the ratio of the number of the isocyanate groups used to the number of the hydroxyl groups used. Preferably, in the polyurethane polymer PUP after the reaction of all hydroxyl groups of the polyol, there preferably remains a content of free isocyanate groups of 0.5 to 15% by weight, more preferably of 0.5 to 10% by weight.

Optionally, the polyurethane polymer PUP can be prepared with additional use of plasticizers, in which case the plasticizers used do not contain any groups reactive toward isocyanates.

The polyols used for the preparation of a polyurethane polymer PUP may, for example, be the following commercial polyols or mixtures thereof.

Polyoxyalkylenepolyols, also known as polyetherpolyols or oligoetherols, which are polymerization products of ethylene oxide, 1,2-propylene oxide, 1,2- or 2,3-butylene oxide, oxetane, tetrahydrofuran or mixtures thereof, possibly polymerized with the aid of a starter molecule with two or more active hydrogen atoms, for example water, ammonia or compounds having a plurality of OH or NH groups, for example 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediois, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, and mixtures of the aforementioned compounds. It is possible to use either polyoxyalkylenepolyols which have a low degree of unsaturation (measured to ASTM D-2849-69 and reported in milliequivalents of unsaturation per gram of polyol (meq/g)), prepared, for example, with the aid of double metal cyanide complex catalysts (DMC catalysts), or polyoxyalkylenepolyols with a higher degree of unsaturation, prepared, for example, with the aid of anionic catalysts such as NaOH, KOH, CsOH or alkali metal alkoxides.

Particularly suitable are polyoxyalkylenediols or polyoxyalkylenetriols, especially polyoxyethylene- and polyoxypropylenediols and -triols.

Especially suitable are polyoxyalkylenediols and -triols having a degree of unsaturation lower than 0.02 meq/g and a molecular weight in the range of 1000-30 000 g/mol, and also polyoxypropylenediols and -triols with a molecular weight of 400-8000 g/mol.

Likewise particularly suitable are so-called ethylene oxide-terminated ("EO-endcapped", ethylene oxide-endcapped) polyoxypropylenepolyols. The latter are specific polyoxypropylenepolyoxyethylenepolyols which are obtained, for example, by further alkoxylating pure polyoxypropylenepolyols, especially polyoxypropylenediols and -triols, with ethylene oxide on completion of the polypropoxylation reaction, and have primary hydroxyl groups as a result.

Styrene-acrylonitrile- or acrylonitrile-methyl methacrylate-grafted polyetherpolyols.

Polyesterpolyols, also known as oligoesterols, prepared, for example, from di- to trihydric alcohols, for example 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the aforementioned alcohols, with organic dicarboxylic acids or the anhydrides or esters thereof, for example succinic acid, glutaric acid, adipic acid, suberic acid, sebacic acid, dodecanedicarboxylic acid, maleic acid, fumaric acid, phthalic acid, isophthalic acid, terephthalic acid and hexahydrophthalic acid, or mixtures of the aforementioned acids, and also polyesterpolyols formed from lactones, for example from $\epsilon$-caprolactone.

Polycarbonatepolyols, as obtainable by reaction, for example, of the abovementioned alcohols—used to form the polyesterpolyols—with dialkyl carbonates, diaryl carbonates or phosgene.

Block copolymers which bear at least two hydroxyl groups and have at least two different blocks with polyether, polyester and/or polycarbonate structure of the type described above.

Polyacrylate- and polymethacrylatepolyols.

Polyhydrocarbonpolyols, also known as oligohydrocarbonols, for example poly-hydroxy-functional ethylene-propylene, ethylene-butylene or ethylene-propylene-diene copolymers, as produced, for example, by Kraton Polymers, or poly-hydroxy-functional copolymers of dienes such as 1,3-butadiene or diene mixtures, and vinyl monomers such as styrene, acrylonitrile or isobutylene, or poly-hydroxy-functional polybutadienepolyols, for example those which are prepared by copolymerization of 1,3-butadiene and allyl alcohol and may also be hydrogenated.

Poly-hydroxy-functional acrylonitrile/butadiene copolymers, as can be prepared, for example, from epoxides or amino alcohols and carboxyl-terminated acrylonitrile/butadiene copolymers (commercially available under the Hycar® CTBN name from Hanse Chemie).

These polyols mentioned preferably have a mean molecular weight of 250-30 000 g/mol, especially of 400-20 000 g/mol, and preferably have a mean OH functionality in the range from 1.6 to 3.

Preferred polyols are polyether-, polyester-, polycarbonate- and polyacrylatepolyols, preferably di- and triols. Particular preference is given to polyetherpolyols, especially polyoxypropylene- and polyoxypropylene-polyoxyethylenepolyols.

In addition to these polyols mentioned, small amounts of low molecular weight di- or polyhydric alcohols, for example 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, 1,1,1-trimethylolethane, 1,1,1-trimethylolpropane, glycerol, pentaerythritol, sugar alcohols such as xylitol, sorbitol or mannitol, sugars such as sucrose, other higher polyhydric alcohols, low molecular weight alkoxylation products of the aforementioned di- and polyhydric alcohols, and mixtures of the aforementioned alcohols, can be used additionally in the preparation of the polyurethane polymer PUP. It is likewise possible to use small amounts of polyols with a mean OH functionality of more than 3, for example sugar polyols.

The polyisocyanates used for the preparation of a polyurethane polymer PUP having isocyanate groups are aromatic or aliphatic polyisocyanates, especially the diisocyanates.

An "aromatic isocyanate" refers to an organic compound which has exclusively aromatic isocyanate groups. An "aromatic" isocyanate group is one which is bonded to an aromatic or heteroaromatic radical. An "aliphatic isocyanate" refers to an organic compound which contains aliphatic isocyanate groups. An "aliphatic" isocyanate group refers to one which is bonded to an aliphatic, cycloaliphatic or arylaliphatic radical.

Suitable aromatic polyisocyanates are, for example, monomeric di- or triisocyanates such as 2,4- and 2,6-tolylene diisocyanate and any mixtures of these isomers (TDI), 4,4'-, 2,4'- and 2,2'-diphenylmethane diisocyanate and any mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), 1,3,5-tris(isocyanatomethyl)benzene, tris(4-isocyanatophenyl)methane, tris(4-isocyanatophenyl) thiophosphate, oligomers and polymers of the aforementioned isocyanates, and any mixtures of the aforementioned isocyanates. Preference is given to MDI and TDI.

Suitable aliphatic polyisocyanates are, for example, monomeric di- or triisocyanates such as 1,4-tetramethylene diisocyanate, 2-methylpenta-methylene 1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine diisocyanate and lysine ester diisocyanate, cyclohexane 1,3- and 1,4-diisocyanate, 1-methyl-2,4- and -2,6-diisocyanatocyclohexane and any mixtures of these isomers (HTDI or $H_6TDI$), 1-isocyanate-3,3,5-trimethyl-5-isocyanatomethylcyclohexane (=isophorone diisocyanate or IPDI), perhydro-2,4'- and -4,4'-diphenylmethane diisocyanate (HMDI or $H_{12}MDI$), 1,4-diisocyanato-2,2,6-trimethylcyclohexane (TMCDI), 1,3- and 1,4-bis(isocyanatomethyl)cyclohexane, m- and p-xylylene diisocyanate (m- and p-XDI), m- and p-tetramethyl-1,3- and -1,4-xylylene diisocyanate (m- and p-TMXDI), bis(1-isocyanato-1-methylethyl)naphthalene, dimer and trimer fatty acid isocyanates such as 3,6-bis(9-isocyanatononyl)-4,5-di(1-heptenyl)cyclohexene (dimeryl diisocyanate), $\alpha,\alpha,\alpha',\alpha',\alpha'',\alpha''$-hexamethyl-1,3,5-mesitylene triisocyanate, oligomers and polymers of the aforementioned isocyanates, and any mixtures of the aforementioned isocyanates. Preference is given to HDI and IPDI.

Preference is given to polyurethane polymers PUP with aromatic isocyanate groups.

In a further embodiment, a suitable polyisocyanate P is a polyisocyanate PI in the form of a monomeric di- or triisocyanate, or of an oligomer of a monomeric diisocyanate, suitable monomeric di- or triisocyanates being, for example, the aforementioned aromatic and aliphatic di- and triisocyanates.

Suitable oligomers of a monomeric diisocyanate are especially the oligomers of HDI, IPDI and TDI. Such oligomers are in practice typically mixtures of substances with different degrees of oligomerization and/or chemical structures. They preferably have a mean NCO functionality of 2.1 to 4.0 and contain especially isocyanurate, iminooxadiazinedione, uretdione, urethane, biuret, allophanate, carbodiimide, uretonimine or oxadiazinetrione groups. They preferably have a low content of monomeric diisocyanates. Commercially available types are especially HDI biurets, for example Desmodur® N 100 and Desmodur® N 3200 (from Bayer), Tolonate® HDB and Tolonate® HDB-LV (from Rhodia) and Duranate® 24A-100 (from Asahi Kasei); HDI isocyanurates, for example Desmodur® N 3300, Desmodur® N 3600 and Desmodur® N 3790 BA (from Bayer), Tolonate® HDT, Tolonate® HDT-LV and Tolonate® HDT-LV2 (from Rhodia), Duranate® TPA-100 and Duranate® THA-100 (from Asahi Kasei) and Coronate® HX (from Nippon Polyurethane); HDI uretdiones, for example Desmodur® N 3400 (from Bayer); HDI iminooxadiazinediones, for example Desmodur® XP 2410 (from Bayer); HDI allophanates, for example Desmodur® VP LS 2102 (from Bayer); IPDI isocyanurates, for example Desmodur® Z 4470 (from Bayer) and Vestanat® T1890/100 (from Evonik); TDI oligomers, for example Desmodur® IL (from Bayer); and mixed isocyanurates based on TDI/HDI, for example Desmodur® HL (from Bayer).

In a further embodiment, the polyisocyanate P is a polyisocyanate PI in the form of a room temperature liquid form of MDI, or of a room temperature liquid form of polymeric MDI (PMDI).

Room temperature liquid forms of MDI (so-called "modified MDI") are mixtures of MDI with MDI derivatives, for example MDI carbodiimides, MDI uretonimines or MDI urethanes. Commercially available types of modified MDI are, for example, Desmodur® CD, Desmodur® PF and Desmodur® PC (from Bayer), Lupranat® MM 103 (from BASF), Isonate® M 143 (from Dow), and Suprasec® 2020 and Suprasec® 2388 (from Huntsman).

Polymeric MDI or PMDI refers to mixtures of MDI and MDI homologs. Commercially available types of PMDI are, for example, Desmodur® VL, Desmodur® VL 50, Desmodur® VL R 10, Desmodur® VL R 20 and Desmodur® VKS 20 F (from Bayer), Lupranat® M 10 R and Lupranat® M 20 R (from BASF), Isonate® M 309, Voranate® M 229 and Voranate M® 580 (from Dow), and Suprasec® 5025, Suprasec® 2050 and Suprasec® 2487 (from Huntsman).

Preferred polyisocyanates PI are PMDI, room temperature liquid forms of MDI, and the oligomers of HDI, IPDI and TDI, especially the isocyanurates.

Particularly preferred polyisocyanates Pt are those having aromatic isocyanate groups.

The most preferred polyisocyanates PI are MDI types, especially those with a high proportion of 2,4'-isomer, and also PMDI, and also room temperature liquid forms of MDI.

In yet a further embodiment, the polyisocyanate P is a mixture consisting of at least one polyurethane polymer PUP and at least one polyisocyanate PI, as described above.

Typically, the polyisocyanate P is present in an amount of 5 to 95% by weight, preferably in an amount of 10 to 90% by weight, based on the overall composition. In filled compositions, i.e. compositions which comprise a filler, the polyisocyanate P is preferably present in an amount of 5 to 60% by weight, especially 10 to 50% by weight, based on the overall composition.

The curable composition comprises, as well as at least one polyisocyanate P, at least one aromatic dialdimine of the formula (I) as described in detail above, or a preferred embodiment thereof.

The dialdimine of the formula (I) is present in the curable composition preferably in a slightly superstoichiometric, stoichiometric or substoichiometric amount, based on the isocyanate groups. The dialdimine of the formula (I) is advantageously present in the composition in such an amount that the ratio between the number of the aldimino groups and the number of the isocyanate groups is 0.1 to 1.1, especially 0.15 to 1.0, more preferably 0.2 to 0.9.

The dialdimines of the formula (I) used may also be mixtures of different dialdimines of the formula (I). More particularly, it is possible to use mixtures of different dialdimines which are prepared proceeding from mixtures of different diamines B of the formula (II) and/or mixtures of different aldehydes ALD of the formula (III).

The curable composition may, in addition to at least one polyisocyanate P and to at least one aromatic dialdimine of the formula (I), comprise further assistants and additives.

The curable composition reacts with water or moisture and is crosslinked as a result. When sufficient water is present to convert a majority of or all isocyanate groups, a cured composition which has good mechanical properties forms. The composition is therefore referred to as "moisture-curing".

The curable composition may be present in the form of a one-component composition or in the form of a two-component composition.

In the present document, a "one-component composition" refers to a curable composition whose constituents are stored in mixed form in the same container, and which is storage-stable at room temperature over a prolonged period, i.e. the application or use properties thereof change only insignificantly, if at all, as a result of the storage, and which cures through the action of moisture after application.

In the present document, a "two-component composition" refers to a curable composition whose constituents are present in two different components which are stored in separate containers and are each storage-stable. Not until just before or during the application of the composition are the two components mixed with one another, and the mixed composition then cures, the curing under some circumstances proceeding or being completed only through the action of moisture.

One-component compositions have the advantage that they are applicable without a mixing operation, whereas two-component compositions have the advantage that they cure more rapidly and may comprise, as constituents, substances which are not storable together with isocyanates.

In one embodiment, the curable composition is in the form of a one-component composition.

A preferred polyisocyanate P in the one-component composition is a polyurethane polymer PUP, or a mixture of a polyurethane polymer PUP and a polyisocyanate PI, as described above.

Suitable assistants and additives for a one-component composition are, for example, the following substances:

plasticizers, for example carboxylic esters such as phthalates, for example dioctyl phthalate, diisononyl phthalate or diisodecyl phthalate, adipates, for example dioctyl adipate, azelates and sebacates, organic phosphoric and sulfonic esters or polybutenes;

nonreactive thermoplastic polymers, for example homo- or copolymers of unsaturated monomers, especially from the group comprising ethylene, propylene, butylene, isobutylene, isoprene, vinyl acetate and alkyl (meth) acrylates, especially polyethylenes (PE), polypropylenes (PP), polyisobutylenes, ethylene-vinyl acetate copolymers (EVA) and atactic poly-α-olefins (APAOs);

solvents;

inorganic and organic fillers, for example ground or precipitated calcium carbonates optionally coated with fatty acids, especially stearates, barite ($BaSO_4$, also known as heavy spar), quartz flours, calcined kaolins, aluminum oxides, aluminum hydroxides, silicas, especially finely divided silicas from pyrolysis processes, carbon blacks, especially industrially produced carbon blacks (referred to hereinafter as "carbon black"), PVC powders or hollow spheres;

fibers, for example of polyethylene;

pigments, for example titanium dioxide or iron oxides;

catalysts which accelerate the hydrolysis of the aldimino groups, especially acids or compounds which are hydrolyzable to acids, for example organic carboxylic acids such as benzoic acid, salicylic acid or 2-nitrobenzoic acid, organic carboxylic anhydrides such as phthalic anhydride, hexahydrophthalic anhydride and hexahydromethylphthalic anhydride, silyl esters of organic carboxylic acids, organic sulfonic acids such as methanesulfonic acid, p-toluenesulfonic acid or 4-dodecyl benzenesulfonic acid, sulfonic esters, other organic or inorganic acids, or mixtures of the aforementioned acids and acid esters;

catalysts which accelerate the reaction of the isocyanate groups with water, especially metal compounds, for example organotin compounds such as dibutyltin diacetate, dibutyltin dilaurate, dibutyltin dichloride, dibutyltin diacetylacetonate and dioctyltin dilaurate, bismuth compounds such as bismuth trioctoate and bismuth tris (neodecanoate), and compounds containing tertiary amino groups, such as 2,2'-dimorpholinodiethyl ether and 1,4-diazabicyclo[2.2.2]octane;

rheology modifiers, for example thickeners or thixotropic agents, for example urea compounds, polyamide waxes, bentonites or fumed silicas;

reactive diluents and crosslinkers, for example monomeric diisocyanates, and also oligomers and derivatives of these diisocyanates, adducts of monomeric diisocyanates with short-chain polyols, and also adipic dihydrazide and other dihydrazides, and also blocked amines in the form of ketimines, oxazolidines, enamines or aldimines not corresponding to the formula (I), which are obtainable proceeding from other amines than the aromatic diamines B of the formula (II) and/or other aldehydes than the aldehydes ALD of the formula (III), especially the polyaldimines described in WO 2004/013088 A1 and especially polyaldimines proceeding from oligomeric forms of diaminodiphenylmethane (PMDA);

desiccants, for example molecular sieves, calcium oxide, high-reactivity isocyanates such as p-tosyl isocyanate, orthoformic esters, tetraalkoxysilanes such as tetraethoxysilane;

organoalkoxysilanes, also referred to hereinafter as "silanes", for example epoxysilanes, (meth)acryloylsilanes, isocyanatosilanes, vinylsilanes, carbamatosilanes, alkylsilanes, S-(alkylcarbonyl)mercaptosilanes and aldiminosilanes, and oligomeric forms of these silanes;

stabilizers against heat, light and UV radiation;

flame-retardant substances;

surface-active substances, for example wetting agents, leveling agents, devolatilizers or defoamers;

biocides, for example algicides, fungicides or substances which inhibit fungal growth.

It is advantageous to ensure that such additives do not impair the storage stability of the composition. This means that these additives must not trigger the reactions which lead to crosslinking, such as hydrolysis of the aldimino groups or crosslinking of the isocyanate groups, to a significant degree during storage. More particularly, this means that all of these additives should contain at most traces of water, if any. It may therefore be advisable to chemically or physically dry certain additives before they are mixed into the composition.

The one-component composition preferably comprises, in addition to at least one polyisocyanate P and at least one aromatic dialdimine of the formula (I), at least one catalyst. More particularly, the composition comprises, as a catalyst, a carboxylic acid such as benzoic acid or salicylic acid and/or a tin compound and/or a bismuth compound. It may be advantageous when different catalysts or different catalyst types, for example an acid and a metal compound, are mixed with one another.

Additionally preferably, the one-component composition comprises, in addition to at least one polyisocyanate P and at least one aromatic dialdimine of the formula (I), at least one further assistant and additive, especially selected from the group comprising plasticizers, crosslinkers, fillers and thickeners.

The one-component composition described is preferably produced and stored with exclusion of moisture. In a suitable package or arrangement impervious to ambient conditions, for example a drum, a pouch or a cartridge, it possesses an excellent storage stability. The terms "storage-stable" and "storage stability" in connection with a curable composition refer, in the present document, to the fact that the viscosity of the composition at a given application temperature and in the course of suitable storage within the period considered rises, if at all, at most to such an extent that the composition remains useable in the manner intended.

When the one-component composition described comes into contact with moisture or water, the aldimino groups of the dialdimine of the formula (I) begin to undergo hydrolysis. The isocyanate groups present in the composition then react with the aldimino groups being hydrolyzed to release the aldehyde ALD of the formula (III). Excess isocyanate groups in relation to the aldimino groups react directly with water. As a result of these reactions, the composition crosslinks and ultimately cures to give a solid material. The reaction of the isocyanate groups with the aldimino groups being hydrolyzed need not necessarily proceed via free amino groups; reactions with intermediates of the hydrolysis reaction are also possible. For example, it is conceivable that an aldimino group being hydrolyzed reacts directly with an isocyanate group in the form of a hemiaminal.

The water required for the curing reaction may either originate from the air (air humidity), or else the composition can be contacted with a water-containing component, for example by spraying, or a water-containing component can be added to the composition in the course of application, especially by mixing it in.

The curing generally proceeds without bubbles, especially also at a high curing rate.

The curing rate can be influenced via the type and amount of one or more catalysts which may be present, by the temperature which exists in the course of curing and by the air humidity or the amount of water added. When a water-containing component is added to the composition, the curing proceeds in a greatly accelerated manner compared to curing exclusively with air humidity. The present invention thus also describes a cured composition.

In a further embodiment, the curable composition is present in the form of a two-component composition. The two-component composition consists of a component K1 and of a component K2, which are stored separately from one another and are mixed with one another only shortly before the application.

In one embodiment of the two-component composition, the polyisocyanate P and the dialdimine of the formula (I) are part of component K1, while component K2 comprises compounds reactive toward isocyanate groups, especially water and/or polyols and/or polyamines and/or amino alcohols and/or polythiols.

In another embodiment of the two-component composition, the polyisocyanate P is part of component K1, while component K2 comprises the dialdimine A of the formula (I) and compounds reactive toward isocyanate groups, especially water and/or polyols and/or polyamines and/or amino alcohols and/or polythiols.

Component K2 preferably comprises at least one dialdimine of the formula (I) and water.

A preferred polyisocyanate P in the two-component composition is a polyisocyanate P1, or a mixture of a polyurethane polymer PUP and a polyisocyanate P1, as already described above.

Suitable polyols in component K2 are the same commercial polyols as already mentioned as suitable for preparation of a polyurethane polymer PUP, and those low molecular weight di- or polyhydric alcohols as already mentioned above as suitable for additional use in the preparation of a polyurethane polymer PUP. Suitable polyamines in component K2 are commercial aliphatic or aromatic polyamines with primary and/or secondary amino groups, as typically used in two-component polyurethane compositions, for example 1,5-diamino-2-methylpentane (MPMD), 1,3-xylylenediamine (MXDA), N,N'-dibutyl-ethylenediamine, 3,5-diethyl-2,4(6)-diaminotoluene (DETDA), 3,5-dimethylthio-2,4(6)-diaminotoluene (Ethacure° 300, Albemarle), and primary and secondary polyoxyalkylenediamines, as obtainable, for example, under the Jeffamine® name (from Huntsman Chemicals). Suitable amino alcohols in component K2 are compounds which have at least one primary or secondary amino group and at least one hydroxyl group, for example 2-aminoethanol, 2-methylamino-ethanol, 1-amino-2-propanol and diethanolamine. Suitable polythiols in component K2 are liquid mercapto-terminated polymers known, for example, under the Thiokol° brand name, and polyesters of thiocarboxylic acids. If component K2 comprises water, it is advantageous when the amount of water corresponds at most to the amount of water required to hydrolyze the dialdimine—and any further blocked amines present. In addition, both components may comprise further assistants and additives as have already been mentioned above for a one-component composition. In the case of component K2, however, still further assistants and additives are additionally also possible. More particularly, these are those assistants and additives which are storable only for a short period, if at all, with aromatic isocyanate groups. In particular, these are catalysts such as:

compounds of zinc, manganese, iron, chromium, cobalt, copper, nickel, molybdenum, lead, cadmium, mercury, antimony, vanadium, titanium, zirconium or potassium, such as zinc(II) acetate, zinc(II) 2-ethylhexanoate, zinc(II) laurate, zinc(II) oleate, zinc(II) naphthenate, zinc(II) acetylacetonate, zinc(II) salicylate, manganese(II) 2-ethylhexanoate, iron(III) 2-ethylhexanoate, iron(III) acetylacetonate, chromium(III) 2-ethylhexanoate, cobalt(II) naphthenate, cobalt(II) 2-ethylhexanoate, copper(II) 2-ethylhexanoate, nickel(II) naphthenate, phenylmercuric neodecanoate, lead(II) acetate, lead(II) 2-ethylhexanoate, lead(II) neodecanoate, lead(II) acetylacetonate, aluminum lactate, aluminum oleate, aluminum(III) acetylacetonate, diisopropoxytitanium bis(ethylacetoacetate), dibutoxytitanium bis(ethylacetoacetate), di-butoxytitanium bis(acetylacetonate), potassium acetate, potassium octanoate; tertiary amines, such as triethylamine, tributylamine, N-ethyldiisopropylamine, N,N,N',N'-tetramethylethylenediamine, pentamethyldiethylenetriamine and higher homologs thereof, N,N,N',N'-tetramethylpropylenediamine, pentamethyldipropylenetriamine and higher homologs thereof, N,N,N',N'-tetramethyl-1,3-butanediamine, N,N,N',N'-tetramethyl-1,6-hexanediamine, bis(dimethylamino)methane, N,N-dimethylbenzylamine, N,N-dimethylcyclohexylamine, N-methyldicyclohexylamine, N,N-dimethylhexadecylamine, bis(N,N-diethylaminoethyl) adipate, N,N-dimethyl-2-phenylethylamine, tris(3-dimethylaminopropyl)amine, 1,4-diazabicyclo[2.2.2]octane (DABCO), 1,8-diazabicyclo[5.4.0]undec-7-ene (DBU), 1,5-diazabicyclo[4.3.0]nonene (DBN) N-methylmorpholine, N-ethylmorpholine, N-cocomorpholine, N,N'-dimethylpiperazine, N-methyl-N'-dimethylaminoethylpiperazine, bis(dimethylaminoethyl)piperazine, 1,3,5-tris(dimethylaminopropyl)hexahydrotriazine, bis(2-dimethylaminoethyl)ether; aromatic nitrogen compounds, such as 4-dimethylaminopyridine, N-methylimidazole, N-vinylimidazole or 1,2-dimethylimidazole; amidines and guanidines, such as 1,1,3,3-tetramethylguanidine; tertiary amines containing active hydrogen atoms, such as triethanolamine, triisopropanolamine, N-methyldiethanolamine, N,N-dimethylethanolamine, 3-(dimethylamino)propyldiisopropanolamine, bis(3-(dimethylamino)propyl)isopropanolamine, bis(3-dimethylaminopropyl)amine, 3-(dimethylamino)propylurea, Mannich bases, such as 2,4,6-tris(dimethylaminomethyl)phenol or 2,4,6-tris(3-(dimethylamino)propylaminomethyl)phenol, N-hydroxypropylimidazole, N-(3-aminopropyl)imidazole, and alkoxylation and polyalkoxylation products of these compounds, for example dimethylaminoethoxyethanol; organic ammonium compounds, such as benzyltrimethylammonium hydroxide, or alkoxylated tertiary amines; so-called "delayed action" catalysts, which are modifications of known metal or amine catalysts, such as reaction products of tertiary amines and carboxylic acids or phenols, for example of 1,4-diazabicyclo[2.2.2]octane or DBU and formic acid or acetic acid; and combinations of the compounds mentioned, especially of metal compounds and tertiary amines.

The two-component composition preferably comprises, in addition to at least one polyisocyanate P and at least one aromatic dialdimine of the formula (I), at least one catalyst. More particularly, the composition comprises, as a catalyst, a carboxylic acid such as benzoic acid or salicylic acid and/or a tin compound and/or a bismuth compound. It may be advantageous when different catalysts or different catalyst types, for example an acid and a metal compound, are mixed with one another.

Additionally preferably, the two-component composition comprises, in addition to at least one polyisocyanate P and at least one aromatic dialdimine of the formula (I), at least one further assistant and additive, especially selected from the group comprising plasticizers, crosslinkers, fillers and thickeners.

Component K2 preferably does not contain any isocyanate groups.

If the two-component composition comprises further blocked amines, especially ketimines, oxazolidines, enamines or aldimines not corresponding to the formula (I), they may be part of component K1 and/or K2; they are preferably part of component K2. The blocked amines have the property of releasing amino groups when they are hydrolyzed, which react rapidly with isocyanate groups present.

The components K1 and K2 described are prepared separately from one another, with exclusion of moisture at least for component K1. The two components K1 and K2 are storage-stable separately from one another, i.e. they can each be stored in a suitable package or arrangement, for example in a vat, a hobbock, a pouch, a bucket or a cartridge, over several months up to one year and longer before they are used, without their particular properties changing to a degree relevant for the use thereof.

The mixing ratio between components K1 and K2 is preferably selected such that the groups reactive toward isocyanate groups in components K1 and K2 are in a suitable ratio relative to the isocyanate groups of component K1. In the two-component composition described, before the curing, suitably 0.1 to 1.1 equivalents, preferably 0.5 to 0.95 equivalent and more preferably 0.6 to 0.95 equivalent of the sum of the groups reactive toward isocyanates is present per equivalent of isocyanate groups, the aldimino groups and any further blocked amino groups present being counted among the groups reactive toward isocyanates, and water not being counted among the groups reactive toward isocyanates. Excess isocyanate groups react especially directly with water, for example with air humidity.

Before or during the application of the two-component composition described, components K1 and K2 are mixed with one another by means of a suitable process. The mixing can be effected continuously or batchwise. The mixed composition is applied during the mixing or after the mixing, by contacting it with a solid surface, optionally by means of a suitable assistant. In doing this, it has to be ensured that not too much time lapses between the mixing of components K1 and K2 and the application, since this can result in problems, for example slowed or incomplete buildup of adhesion to the solid surface. The maximum period within which the mixed composition should be applied is referred to as the "pot life" or else as the "open time". Often, the open time is defined as the time within which the viscosity of the mixed composition doubles.

After the mixing of components K1 and K2, the curing commences. The dialdimine of the formula (I) begins to hydrolyze in the manner already described and to react with the isocyanate groups as soon as it comes into contact with water. The water is either already present in the mixed composition—by virtue of it having been a constituent of component K2, or by virtue of it having been added to the composition before or during the mixing of components K1 and K2—or the water diffuses into the mixed composition in the form of air humidity. In the latter case, the dialdimine reacts with the isocyanate groups from the outside inward, in parallel to the penetration of the air humidity into the composition. As already described, the reaction of the isocyanate groups with the aldimino groups being hydrolyzed need not necessarily proceed via free amino groups, but can also proceed via intermediates of the hydrolysis reaction. In the same way, the reactive groups are released from further latent hardeners which may be present in the composition. In addition, after the mixing of components K1 and K2, any compounds which are reactive toward isocyanate groups and are present in the composition, such as especially polyols and polyamines, react with the isocyanate groups. Excess isocyanate groups react especially directly with water. As a result of these reactions, the mixed composition crosslinks and ultimately cures to a solid material. The present invention thus also describes a cured composition.

The curing generally proceeds without bubbles, especially also at a high curing rate.

The curing rate can be influenced via the type and amount of one or more catalysts which may be present, via the temperature which prevails in the course of curing, and via the air humidity or the amount of water introduced via component K2.

The curable compositions described, comprising at least one polyisocyanate P and at least one aromatic dialdimine of the formula (I), have a whole series of advantageous properties.

They are producible in a simple process, especially owing to the fact that the dialdimines of the formula (I) are liquid at room temperature. As dialdimines of the formula (I), high-melting primary aromatic diamines, such as 1,4-phenylenediamine in particular, are now present in a form suitable for use in a curable composition, which have to date been useable only with great difficulty, if at all, in room temperature processable, especially solvent-free, polyurethane compositions. Curable compositions which comprise low-viscosity dialdimines of the formula (I) have an advantageous consistency with a relatively low intrinsic viscosity, which enables good processability of the composition for many applications.

In addition, the curable compositions described have good storage stability, especially also when the dialdimines of the formula (I) are stored together with the polyisocyanate P. Also for the preferred case that the polyisocyanate P has aromatic isocyanate groups, the storage stability together with dialdimines of the formula (I) is good.

In addition, the curable compositions described have only a very low odor, or are entirely odorless, before, during and after the curing, which is generally not the case in the presence of aldehydes. Compositions which comprise, as dialdimines of the formula (I), exclusively the preferred dialdimines derived from aldehydes ALD1 of the formula (III a) are odorless before, during and after the curing, provided of course that they do not contain any other constituents with a strong odor.

In addition, the curable compositions described, especially in the form of one-component compositions, have a relatively long open time. Surprisingly, the curing rate of these compositions is, however, in spite of the relatively long open time, no longer than, for example, the curing rate of corresponding compositions comprising aliphatic dialdimines, which are produced proceeding from aliphatic amines. The combination of long open time and rapid curing is extremely desirable in practice for many one-component and two-component applications. Thus, the application of a one-component composition is often simpler when a little time remains after the application thereof to bring the composition into the desired form before a skin of partly cured material has formed on the surface. The use of a two-component composition is also often significantly simpler when it has a prolonged open time, given that both the mixing operation and the application of the composition, and any further working steps needed, for example in order to bring the composition into the desired form, have to be effected within the open time. Subsequently, the composition should, however, cure rapidly in order to be subjectable to load as soon as possible. In the case that a one-component composition described is cured in an accelerated manner with a water-containing component, the relatively long open time has a particularly advantageous effect, since the time window available for the application in such accelerated systems is generally very short.

The curable compositions described generally cure without the formation of bubbles. This is also true in the case of a high curing rate.

In addition, the curable compositions described have, in the cured state, good mechanical properties and good stability to heat and moisture. The preferred compositions comprising an aromatic polyisocyanate P have a particularly good stability to heat and moisture, and particularly good mechanical properties, especially a high strength coupled with a high extensibility. The good thermal stability can possibly be attributed to the fact that the urea groups which form in the curing reaction of the aromatic isocyanate groups with the aromatic aldimino groups are aromatically substituted on both sides and therefore do not exhibit any tendency to exchange the substituents.

Curable compositions comprising at least one polyisocyanate P and at least one of the particularly preferred dialdimines of the formula (I) proceeding from 1,4-phenylenediamine and an aldehyde ALD1 of the formula (III a) have particularly advantageous properties. They are producible in a particularly simple manner owing to the fact that these dialdimines of the formula (I) are odorless low-viscosity liquids, and they have particularly good mechanical properties in the cured state, especially particularly high strengths, especially when the polyisocyanate P is an aromatic polyisocyanate P. A further advantage of these compositions is that the aldimines of the formula (I) derived from 1,4-phenylenediamine have a reactivity toward isocyanates which is comparatively high for aromatic amines, which leads to a comparatively short skin formation time of the compositions. Another advantage, finally, consists in the fact that the parent 1,4-phenylenediamine of the dialdimine has a low toxicity for aromatic amines, which is expressed, for example, by the fact that it is classified neither as mutagenic nor as carcinogenic.

With the inventive curable compositions, it is possible to obtain one- and two-component polyurethane compositions which cure in a formal sense through primary aromatic diamines, especially primary aromatic diamines with little steric hindrance, if any, which are as such relatively high-melting and often sparingly soluble solids and are therefore barely useable in practice. More particularly, the polyurethane compositions can be cured in a formal sense via the particularly high-melting and sparingly soluble 1,4-phenylenediamine. Cured polyurethane compositions with urea bonds which are formed in a formal sense from 1,4-phenylenediamine and aromatic isocyanate groups have a particularly high strength and a particularly good stability to heat and moisture.

Preferred applications of the curable compositions described are adhesives, sealants, potting compositions, coatings, floor coverings, paints, lacquers, primers or foams.

The curable composition described is especially suitable as a one-component or two-component elastic adhesive with high demands on the mechanical properties, such as high moduli of elasticity coupled with a high extensibility, and also for a one-component or two-component coating, especially a floor covering, with high crack bridging.

The curable composition described is especially suitable as an adhesive in motor vehicle construction, especially for the adhesive bonding of window panes.

A further aspect of the present invention relates to a process for adhesive bonding a substrate S1 to a substrate S2, which comprises the steps of:
i) applying an above-described curable composition to a substrate S1;
ii) contacting the applied composition with a substrate S2 within the open time of the composition;
or
i') applying an above-described curable composition to a substrate S1 and to a substrate S2;
ii') contacting the applied compositions with one another within the open time of the composition;
where the substrate S2 consists of the same material as, or a different material than, the substrate S1.

A further aspect of the present invention relates to a process for sealing. This comprises the step of:
i") applying an above-described curable composition between a substrate S1 and a substrate S2, such that the composition is in contact with the substrate S1 and the substrate S2;
where the substrate S2 consists of the same material as, or a different material than, the substrate S1.

The composition is typically injected into a joint.

A further aspect of the present invention relates to a process for coating a substrate S1. This comprises the step of:
i'") applying an above-described curable composition to a substrate S1 within the open time of the composition.

In these three processes, suitable substrates S1 and/or S2 are, for example, inorganic substrates such as glass, glass ceramic, concrete, mortar, brick, tile, gypsum and natural stone such as granite or marble; metals or alloys such as aluminum, steel, nonferrous metals, galvanized metals; organic substrates such as leather, fabrics, paper, wood, resin-bound woodbase materials, resin-textile composite materials, plastics such as polyvinyl chloride (rigid and flexible PVC), acrylonitrile-butadiene-styrene copolymers (ABS), SMC (sheet molding composites), polycarbonate (PC), polyimide (PA), polyesters, PMMA, polyesters, epoxy resins, polyurethanes (PU), polyoxymethylene (POM), polyolefins (PO), especially surface-plasma-, -corona- or -flame-treated polyethylene (PE) or polypropylene (PP), ethylene/propylene copolymers (EPM) and ethylene/propylene-diene terpolymers (EPDM); coated substrates such as powder-coated metals or alloys; and paints and coating materials, especially automotive coating materials.

The substrates can be pretreated if required before the application of the composition. Such pretreatments include especially physical and/or chemical cleaning processes, for example grinding, sandblasting, brushing or the like, or treatment with detergents or solvents, or the application of an adhesion promoter, of an adhesion promoter solution or of a primer.

In the case of a two-component composition, the two components K1 and K2 are mixed with one another shortly before application.

The described curable composition for adhesive bonding and/or sealing of substrates S1 and/or S2 is applied typically from commercially available cartridges which, for smaller applications, are preferably operated manually. Application by means of compressed air from a cartridge or from a vat or hobbock by means of a delivery pump or of an extruder, if appropriate by means of an application robot, is likewise possible. Such application methods are preferred especially in applications in industrial manufacture or in the case of large applications.

The curable composition can be applied within a broad temperature spectrum. For example, the composition can be applied at room temperature, as is typical of an elastic adhesive or a sealant. The composition can, however, also be applied at lower or else higher temperatures. The latter is advantageous especially when the composition comprises proportions of high-viscosity or meltable components, as are typically present in meltable adhesives, for example warm-melt adhesives or hot-melt adhesives.

The described processes for adhesive bonding, sealing or coating—or the use of one of the curable compositions described as an adhesive, sealant, potting composition, coating, floor covering, paint, coating material, primer or foam—give rise to an article.

This article is especially a built structure, especially a built structure in construction or civil engineering, or an industrial good or a consumer good, especially a window, a domestic appliance, or a mode of transport, especially a water or land vehicle, preferably an automobile, a bus, a truck, a train or a ship, or an installable component of a mode of transport, or an article in the furniture, textile or packaging industry.

EXAMPLES

1. Description of the Test Methods

Infrared spectra were measured on a Perkin-Elmer 1600 FT-IR instrument as undiluted films on a horizontal ATR analysis unit with a ZnSe crystal, and solid substances were melted for application; the absorption bands are reported in wavenumbers ($cm^{-1}$) (measurement window: 4000-650 $cm^{-1}$); the addition sh indicates a band which appears as a shoulder, the addition br a broad band.

$^1$H NMR spectra were measured on a Bruker DPX-300 spectrometer at 300.13 MHz; the chemical shifts δ are reported in ppm relative to tetramethylsilane (TMS), coupling constants J are reported in Hz; true and pseudo coupling patterns were not distinguished.

The viscosity was measured on a Physica UM thermostated cone-plate viscometer (cone diameter 20 mm, cone angle 1°, cone tip-plate distance 0.05 mm, shear rate 10 to 1000 $s^{-1}$), as described in DIN EN ISO 3219.

The amine content, i.e. the total content of free amino groups and aldimino groups in the dialdimines prepared, was determined by titrimetric means (with 0.1N $HClO_4$ in glacial acetic acid, against crystal violet) and is always reported in mmol N/g.

2. Preparation of Dialdimines

Example 1

Dialdimine A-1

In a round-bottom flask, under a nitrogen atmosphere, 5.00 g of 2,4-diaminotoluene (amine content 16.33 mmol N/g; melting point 98-100° C.) were suspended in 24.26 g of 2,2-dimethyl-3-lauroyloxypropanal. The mixture was heated and evacuated over 90 minutes (10 mbar, 80-100° C.), in the course of which a homogeneous liquid formed. Yield: 27.7 g of a reddish-brown, odorless oil with an amine content of 2.94 mmol N/g and a viscosity of 160 mPa·s at 20° C.

IR: 2954, 2922, 2852, 1736 (C=O), 1652 (C=N), 1600, 1572, 1492, 1466, 1419, 1392, 1374, 1366, 1349sh, 1302, 1246, 1156, 1110, 1074, 1022, 998, 934, 872, 822, 808sh, 766, 758, 720.

$^1$H NMR ($CDCl_3$, 300 K): δ 7.73 and 7.66 (2×s, 2×1H, CH=N), 7.09 (dd, J=7.8/0.4, 1H, Ar—$H^6$), 6.71 (dd, J=7.8/2.2, 1H, Ar—$H^5$), 6.40 (d, J=2.2, 1H, Ar—$H^3$), 4.16 and 4.13 (2×s, 2×2 H, C($CH_3$)$_2$—$CH_2$—O), 2.20 (s, 3H, Ar—$CH_3$), 2.31 (2×t, J=7.5, 4 H, OC(O)—$CH_2$—$CH_2$), 1.61 (m, 4H, OC(O)—$CH_2$—$CH_2$), 1.23 (m, 32H, $CH_3$—($CH_2$)$_8$—$CH_2$—$CH_2$—CO), 1.22 (s, 12H, C($CH_3$)$_2$—$CH_2$—O), 0.88 (t, J=6.7, 6 H, $CH_3$—($CH_2$)$_{10}$—CO).

Example 2

Dialdimine A-2

In a round-bottom flask, under a nitrogen atmosphere, 5.00 g of 3,4-diaminotoluene (amine content 16.20 mmol N/g; melting point 87-89° C.) were suspended in 24.26 g of 2,2-dimethyl-3-lauroyloxypropanal. The mixture was heated and evacuated over 90 minutes (10 mbar, 80° C.), in the course of which a homogeneous liquid formed. Subsequently, the temperature was increased to 100° C. and evacuation was effected under high vacuum for a further 60 minutes. Yield: 27.8 g of a dark brown, odorless oil with an amine content of 1.40 mmol N/g and a viscosity of 210 mPa·s at 20° C.

IR: 3370br, 2954, 2922, 2852, 1736 (C=O), 1652 (C=N), 1608, 1583, 1508, 1492, 1466, 1418, 1393, 1374, 1366sh, 1350sh, 1301, 1282sh, 1248, 1236, 1158, 1114, 1074, 1020, 1000, 932, 870, 834, 806, 778, 722.

Example 3

Dialdimine A-3

Under the same conditions as described in Example 1, 5.00 g of 1,3-phenylenediamine (amine content 18.43 mmol N/g; melting point 64-66° C.) were reacted with 27.62 g of 2,2-dimethyl-3-lauroyloxypropanal. Yield: 30.7 g of a pale yellow, odorless oil with an amine content of 2.95 mmol N/g and a viscosity of 190 mPa·s at 20° C.

IR: 3060, 2955, 2922, 2852, 1736 (C=O), 1652 (C=N), 1592, 1466, 1418, 1392, 1374, 1366, 1349sh, 1302sh, 1282sh, 1248, 1236sh, 1156, 1112, 1076, 1022, 998, 934, 874, 816sh, 780, 722, 696.

$^1$H NMR ($CDCl_3$, 300 K): δ 7.74 (s, 2H, CH=N), 7.26 (td, J=7.9/0.4, 1H, Ar—$H^5$), 6.81 (dd, J=7.9/2.0, 2H, Ar—$H^{4,6}$), 6.63 (td, J=2.0/0.4, 1H, Ar—$H^2$), 4.14 (s, 4H, C($CH_3$)$_2$—$CH_2$—O), 2.31 (t, J=7.5, 4H, OC(O)—$CH_2$—$CH_2$), 1.61 (m, 4H, OC(O)—$CH_2$—$CH_2$), 1.24 (m, 32H, $CH_3$—($CH_2$)$_8$—$CH_2$—$CH_2$—CO), 1.22 (s, 12H, C($CH_3$)$_2$—$CH_2$—O), 0.88 (t, J=6.7, 6H, $CH_3$—($CH_2$)$_{10}$—CO).

Example 4

Dialdimine A-4

Under the same conditions as described in Example 1, 5.00 g of 1,4-phenylenediamine (amine content 18.40 mmol N/g; melting point 138-143° C.) were reacted with 27.62 g of 2,2-dimethyl-3-lauroyloxypropanal. Yield: 30.7 g of a pale yellow, odorless oil with an amine content of 3.00 mmol N/g and a viscosity of 170 mPa·s at 20° C.

IR: 3031, 2954, 2922, 2852, 1736 (C=O), 1648 (C=N), 1604sh, 1573, 1496, 1466, 1418, 1392, 1374, 1366, 1347sh, 1298sh, 1282sh, 1249, 1231sh, 1206, 1156, 1110, 1072, 1022, 998, 936, 867, 846, 811, 770, 722.

$^1$H NMR ($CDCl_3$, 300 K): δ 7.73 (s, 2H, CH=N), 6.98 (s, 4H, Ar—H), 4.14 (s, 4H, C($CH_3$)$_2$—$CH_2$—O), 2.31 (t, J=7.5, 4H, OC(O)—$CH_2$—$CH_2$), 1.61 (m, 4H, OC(O)—$CH_2$—$CH_2$), 1.25 (m, 32H, $CH_3$—($CH_2$)$_8$—$CH_2$—$CH_2$—CO), 1.22 (s, 12H, C($CH_3$)$_2$—$CH_2$—O), 0.88 (t, J=6.7, 6H, $CH_3$—($CH_2$)$_{10}$—CO).

Example 5

Dialdimine A-5

Under the same conditions as described in Example 1, 10.00 g of 4,4'-diaminodiphenylmethane (amine content 10.00 mmol N/g; melting point 89-91° C.) were reacted with 29.87 g of 2,2-dimethyl-3-lauroyloxypropanal. Yield: 38.0 g of an amber, odorless oil with an amine content of 2.64 mmol N/g and a viscosity of 340 mPa·s at 20° C.

IR: 3022, 2954, 2922, 2851, 1735 (C=O), 1649 (C=N), 1606, 1572, 1504, 1466, 1416, 1392, 1373, 1366, 1295, 1248, 1208, 1158, 1110, 1074, 1016, 998, 934, 918, 865, 846, 820, 770, 720.

¹H NMR (CDCl₃, 300 K): δ 7.71 (s, 2H, CH=N), 7.13 and 6.92 (2×m, 2×4 Ar—H), 4.13 (s, 4H, C(CH₃)₂—CH₂—O), 3.95 (s, 2H, Ar—CH₂—Ar), 2.30 (t, J=7.5, 4H, OC(O)—CH₂—CH₂), 1.60 (m, 4H, OC(O)—CH₂—CH₂), 1.25 (m, 32H, CH₃—(CH₂)₈—CH₂—CH₂—CO), 1.21 (s, 12H, C(CH₃)₂—CH₂—O), 0.88 (t, J=6.7, 6H, CH₃—(CH₂)₁₀—CO).

Example 6

Dialdimine A-6

Under the same conditions as described in Example 1, 10.00 g of 4,4'-diamino-3,3'-dichlorodiphenylmethane (MOCA; amine content 7.43 mmol N/g; melting point 102-107° C.) were reacted with 22.36 g of 2,2-dimethyl-3-lauroyloxypropanal. Yield: 31.1 g of a yellow, odorless oil with an amine content of 2.36 mmol N/g and a viscosity of 780 mPa·s at 20° C.

IR: 3468br, 3380br, 3027, 2953, 2922, 2852, 2716br, 1734 (C=O), 1658 (C=N), 1625, 1603sh, 1556, 1506, 1486, 1466, 1417, 1398, 1374, 1366, 1308, 1250, 1224, 1156, 1112, 1075, 1056, 1022, 1000, 932, 905, 896sh, 874, 830, 810, 774, 722, 694sh, 686.

¹H NMR (CDCl₃, 300 K): δ 7.68 (t, J=1.0, 2H, CH=N), 7.16 (2×d, J=1.7, 2H, Ar—H²), 7.00 (dd, J=8.0/1.7, 2H, Ar—H⁶), 6.75 (d, J=8.0, 2H, Ar—H⁵), 4.15 (s, 4H, C(CH₃)₂—CH₂—O), 3.87 (s, 2H, Ar—CH₂—Ar), 2.31 (t, J=7.5, 4H, OC(O)—CH₂—CH₂), 1.61 (m, 4H, OC(O)—CH₂—CH₂), 1.24 (m, 44H, CH₃—(CH₂)₈—CH₂—CH₂—CO and C(CH₃)₂—CH₂—O), 0.88 (t, J=6.7, 6H, CH₃—(CH₂)₁₀—CO).

Comparative Example 7

Dialdimine A-7

In a round-bottom flask, under a nitrogen atmosphere, 1.79 g of 1,4-phenylenediamine (1,4-PDA; amine content 18.40 mmol N/g; melting point 138-143° C.) were suspended in 5.00 g of 3-acetoxy-2,2-dimethylpropanal. To this were added 20 ml of dichloromethane, and the mixture was stirred at room temperature over 10 minutes, in the course of which the amine dissolved completely and the initially clear solution became increasingly turbid. The reaction mixture was evacuated over 90 minutes (5·10⁻² mbar, 80-100° C.). This gave 5.91 g of a light brown, intensely odorous solid with an amine content of 5.54 mmol N/g and a melting point of 71-72° C. (Tottoli, uncorrected).

IR: 3027, 2968, 2943sh, 2870, 2846sh, 2715br, 1881br, 1736 (C=O), 1646 (C=N), 1600sh, 1570, 1494, 1470, 1435sh, 1394, 1372, 1228, 1104, 1038, 1008, 986, 928, 867, 842, 812, 793sh, 770, 728.

Comparative Example 8

Dialdimine A-8

Under the same conditions as described in Example 1, 5.00 g of trans-1,4-diaminocyclohexane (amine content 17.25 mmol N/g; melting point 68-72° C.) were reacted with 25.76 g of 2,2-dimethyl-3-lauroyloxypropanal. Yield: 28.7 g of a brownish-white, crystalline and odorless solid with an amine content of 2.92 mmol N/g and a melting point of 47-50° C. (Tottoli, uncorrected).

IR: 2953sh, 2922, 2852, 2824sh, 1736 (C=O), 1664 (C=N), 1466, 1454sh, 1418, 1394, 1376, 1364sh, 1346, 1304, 1248, 1232, 1158, 1110, 1086, 1020, 1000, 942, 894, 887sh, 769, 722, 668.

¹H NMR (CDCl₃, 300 K): δ 7.58 (s, 2H, CH=N), 4.01 (s, 4H, C(CH₃)₂—CH₂—O), 2.95 (m, 2H, N—CH$^{Cy}$), 2.29 (t, J=7.5, 4H, OC(O)—CH₂—CH₂), 1.60 (m, 4H, OC(O)—CH₂—CH₂), 1.26 (m, 32H, CH₃—(CH₂)₈—CH₂—CH₂—CO), 1.08 (s, 12H, C(CH₃)₂—CH₂—O), 0.88 (t, J=6.7, 6H, CH₃—(CH₂)₁₀—CO).

Comparative Example 9

Dialdimine A-9

A round-bottom flask was initially charged under a nitrogen atmosphere with 52.4 g (0.18 mol) of distilled 2,2-dimethyl-3-lauroyloxypropanal. While stirring vigorously, 10.0 g (0.17 mol of N) of 1,6-hexamethylenediamine (BASF; amine content 17.0 mmol N/g) were added slowly from a heated dropping funnel. Thereafter, the volatile constituents were removed under reduced pressure (10 mbar, 80° C.). Yield: 57.7 g of a clear, pale yellow and odorless oil with an amine content of 2.85 mmol N/g.

Example 10

Dialdimine A-10

Under the same conditions as described in Example 1, 10.00 g of 4,4'-diaminodiphenylmethane (amine content: 10.00 mmol N/g; melting point 89-91° C.) were reacted with 22.50 g of 2,2-dimethyl-3-heptanoyloxypropanal. Yield: 30.00 g of an amber, low-odor oil with an amine content of 3.33 mmol N/g and a viscosity of 410 mPa·s at 20° C., which was still mobile at 5° C.

IR: 3024, 2956, 2926, 2858, 1734 (C=O), 1650 (C=N), 1606, 1572, 1504, 1468, 1458sh, 1436sh, 1416, 1392, 1374, 1366, 1316sh, 1294, 1234, 1208, 1160, 1102, 1054, 1025sh, 1016, 994, 934, 916, 865, 846, 820, 772, 726, 713sh.

Comparative Example 11

Dialdimine A-11

As a comparative example, Example 10 of DE 31 33 769 A1 was prepared from 4,4'-diaminodiphenylmethane and 3-(2-methylpropane-carbonyloxy)-2,2-dimethylpropanal. This formed an amber, intensely odorous oil with a viscosity of 2040 mPa·s at 20° C., which was honey-like at 5° C.

3. Production of One-Component Compositions

Examples 12 to 18 and Comparative Examples 19 to 21

In a screwtop polypropylene beaker, the polymer P-1, the preparation of which is described below, was mixed by means of a centrifugal mixer (SpeedMixer™ DAC 150, FlackTek Inc.; 1 min at 2500 rpm) with the ingredients listed in Table 1 in the proportions by weight specified to give a homogeneous material. For comparative example 19, the polymer P-1 and the dialdimine A-8 were heated to 80° C. before the mixing, such that the dialdimine A-8 was in liquid form.

The polymer P-1 was prepared as follows:

4000 g of polyoxypropylenediol (Acclaim® 4200 N, Bayer; OH number 28.5 mg KOH/g) and 520 g of 4,4'-methylenediphenyl diisocyanate (MDI; Desmodur® 44 MC L, Bayer) were reacted at 80° C. to give an NCO-terminated polyurethane polymer with a content of free isocyanate groups of 1.90% by weight.

In all dialdimine-containing compositions, the ratio between the isocyanate groups and the aldimino groups was 1.0/0.7.

through-curing was determined by pouring the composition as a film in a layer thickness of 5 mm into a PTFE mold, storing it under standard climatic conditions and, by periodically raising the film edge, determining the time in days taken for the film to be detachable without residue for the first time from the mold.

TABLE 1

Composition of Examples 12 to 18 and of comparative examples 19 to 21.

| | Example | | | | | | | | | |
|---|---|---|---|---|---|---|---|---|---|---|
| | 12 | 13 | 14 | 15 | 16 | 17 | 18 | 19 (comp.) | 20 (comp.) | 21 (comp.) |
| Polymer P-1 | 50.0 | 50.0 | 50.0 | 50.0 | 50.0 | 50.0 | 50.0 | 50.0 | 50.0 | 50.0 |
| Dialdimine | A-1, 5.4 | A-2, 5.4 | A-3, 5.3 | A-4, 5.3 | A-5, 6.0 | A-6, 6.7 | A-10, 4.8 | A-8, 5.4 | — | A-11, 4.3 |
| Acid catalyst[a] | 0.5 | 0.5 | 0.5 | 0.5 | 0.5 | 0.5 | 0.5 | 0.5 | 0.5 | 0.5 |

[a]5% by weight of salicylic acid in dioctyl adipate.

The compositions thus obtained were tested for viscosity, storage stability, skin formation time, curing rate, bubble formation, mechanical properties and stability to thermal stress.

Storage stability was determined via the change (increase) in viscosity during storage under hot conditions. To this end, the composition was stored at 60° C. in a closed tube in an oven, and the viscosity was measured at 20° C. for a first time after 6 hours and for a second time after 7 days. The storage stability is calculated from the percentage increase in the second viscosity value relative to the first.

To measure the skin formation time ("tack-free time"), a few grams of the composition at room temperature, which had been stored at 60° C. over 6 hours, were applied to cardboard in a layer thickness of approx. 2 mm, and the time taken until, when the surface of the composition is tapped lightly by means of an LDPE pipette, no residues remained any longer on the pipette for the first time was measured under standard climatic conditions (23±1° C. and 50±5% relative air humidity).

The measure employed for the curing rate was the time taken for the composition to cure through. The time until Bubble formation was determined qualitatively with reference to the number of bubbles which occurred during the curing of the composition.

The mechanical properties measured were the tensile strength (breaking force), the elongation at break and the modulus of elasticity of the cured composition. For this purpose, the composition at room temperature, which had been stored at 60° C. over 6 hours, was cast in a planar PTFE mold to a film of thickness approx. 2 mm, which was cured under standard climatic conditions over 7 days. Dumbbells with a length of 75 mm were punched out of the film, with a central element length of 30 mm and a central element width of 4 mm, and tested according to DIN EN 53504 at a pulling speed of 200 mm/min. Some of the dumbbells were stored before the measurement of the mechanical properties at 100° C. in an oven over 7 days and then under standard climatic conditions for 24 hours in order to test the stability to thermal stress of the cured composition.

The results of the tests are listed in Table 2.

TABLE 2

Properties of examples 12 to 18 and of comparative examples 19 to 21.

| | Example | | | | | | | | | |
|---|---|---|---|---|---|---|---|---|---|---|
| | 12 | 13 | 14 | 15 | 16 | 17 | 18 | 19 (comp.) | 20 (comp.) | 21 (comp.) |
| Viscosity after 6 h[a] | 38 | 41 | 37 | 34 | 40 | 50 | 36 | 31 | 48 | 42 |
| Viscosity after 7 d[a] | 45 | 73 | 40 | 37 | 44 | 66 | 40 | 33 | 52 | 49 |
| $\Delta_{Viscosity}$ (%)[b] | 18 | 78 | 8 | 9 | 10 | 32 | 11 | 6 | 8 | 17 |
| Skin formation time (min) | 230 | 300 | 270 | 45 | 85 | 900 | 145 | 15 | 360 | 175 |
| Through-curing (d) | 2.5 | 3 | 2 | 2 | 2 | 3.5 | 3 | 2.5 | 3 | 3 |
| Bubble formation | none | none | none | none | none | none | none | none | many | none |
| Tensile strength (MPa)[c] | 3.1 | 1.8 | 6.7 | 6.3 | 3.0 | 3.0 | 3.5 | 6.0 | n.m. | 2.3 |
| | 3.7 | 1.7 | 5.7 | n.d. | n.d. | 3.4 | n.d. | 4.0 | | n.d. |
| Elongation at break (%)[c] | 880 | 560 | 960 | 950 | 870 | 970 | 990 | 650 | n.m. | 800 |
| | 870 | 530 | 1030 | 980 | 600 | n.d. | n.d. | 340 | | n.d. |
| Modulus of elasticity at 0.5-5% extension (MPa)[c] | 4.2 | 3.4 | 3.9 | 13.0 | 8.6 | 1.8 | 6.8 | 12.7 | n.m. | 6.3 |
| | 3.9 | 3.3 | 4.2 | 11.5 | 8.8 | n.d. | n.d. | 9.9 | | n.d. |

[a]in Pa · s, after storage at 60° C., measured at 20° C.
[b]$\Delta_{Viscosity}$ = [(viscosity after 7 d/viscosity after 6 h) − 1] × 100%.
[c]upper figure: testing after curing under standard climatic conditions; lower figure: testing after thermal stress on the cured material (7 d/100° C.).
n.d. = not determined; n.m. = not measurable owing to excessive bubbles.

It is clear from Table 2 that the inventive compositions of Examples 12 to 18, which comprise dialdimines of the formula (I) derived from aromatic diamines, compared to the compositions of comparative example 19, which comprises a dialdimine derived from a cycloaliphatic diamine, a significantly longer skin formation time combined with similar curing rate, and a better stability to thermal stress. The inventive compositions have an adequate to very good storage stability, cure without bubbles and possess outstanding mechanical properties. Example 15, which comprises a dialdimine of 1,4-phenylenediamine, has a very particularly notable profile of properties.

Examples 22 to 26 and Comparative Examples 27 and 28

In a screwtop polypropylene beaker, the polymer P-2, the preparation of which is described below, was mixed by means of a centrifugal mixer (SpeedMixer™ DAC 150, FlackTek Inc.; 1 min at 2500 rpm) with the ingredients listed in Table 3 in the proportions by weight specified to give a homogeneous material.

The polymer P-2 was prepared as follows:

1800 g of dewatered polyoxypropylenediol (Acclaim° 4200 N, Bayer; OH number 28.5 mg KOH/g), 500 g of dewatered polyoxypropylenetriol (Acclaim® 6300, Bayer; OH number 28.0 mg KOH/g) and 200 g of tolylene diisocyanate (TDI; Desmodur® T 80 P, Bayer) were reacted at 80° C. to give an NCO-terminated polyurethane polymer with a content of free isocyanate groups of 1.89% by weight.

In all dialdimine-containing compositions, the ratio between the isocyanate groups and the aldimino groups is 1.0/0.7.

TABLE 3

Composition of Examples 22 to 26 and of comparative examples 27 and 28.

| | Example | | | | | | |
|---|---|---|---|---|---|---|---|
| | 22 | 23 | 24 | 25 | 26 | 27 (comp.) | 28 (comp.) |
| Polymer P-2 | 50.0 | 50.0 | 50.0 | 50.0 | 50.0 | 50.0 | 50.0 |
| Dialdimine | A-1, 5.3 | A-3, 5.3 | A-4, 5.2 | A-5, 6.0 | A-6, 6.7 | A-9, 5.5 | — |
| Acid catalyst[a] | 0.5 | 0.5 | 0.5 | 0.5 | 0.5 | 0.5 | 0.5 |

[a] 5% by weight of salicylic acid in dioctyl adipate.

The compositions thus obtained were tested, as described for Example 12, for viscosity, storage stability, skin formation time, bubble formation, mechanical properties and stability to thermal stress. The results of the tests are listed in Table 4.

TABLE 4

Properties of Examples 22 to 26 and of comparative examples 27 and 28.

| | Example | | | | | | |
|---|---|---|---|---|---|---|---|
| | 22 | 23 | 24 | 25 | 26 | 27 (comp.) | 28 (comp.) |
| Viscosity after 6 h[a] | 19.7 | 19.4 | 18.7 | 18.8 | 23.4 | 15.2 | 21.6 |
| Viscosity after 7 d[a] | 23.0 | 21.0 | 20.6 | 20.1 | 26.7 | 17.2 | 23.7 |
| $\Delta_{Viscosity}$ (%)[b] | 17 | 8 | 10 | 7 | 14 | 13 | 10 |
| Skin formation time (min) | 450 | 360 | 80 | 210 | >720 | 20 | >720 |
| Bubble formation | none | none | none | none | none | none | many |
| Tensile strength (MPa)[c] | 4.7 / 4.8 | 3.4 / 5.0 | 7.0 / 7.6 | 7.5 / n.d. | 4.4 / n.d. | 6.7 / 5.0 | n.m. |
| Elongation at break (%)[c] | 800 / 770 | 650 / 620 | 830 / 710 | 850 / n.d. | 740 / n.d. | 870 / 780 | n.m. |
| Modulus of elasticity at 0.5-5% extension (MPa)[c] | 4.0 / 4.7 | 5.2 / 6.2 | 9.1 / 9.4 | 6.9 / n.d. | 2.6 / n.d. | 2.7 / 2.1 | n.m. |

[a] in Pa · s, after storage at 60° C., measured at 20° C.

[b] $\Delta_{Viscosity}$ = [(viscosity after 7 d/viscosity after 6 h) − 1] × 100%.

[c] upper figure: testing after curing under standard climatic conditions; lower figure: testing after thermal stress on the cured material (7 d/100° C.).

n.d. = not determined; n.m. = not measurable owing to excessive bubbles.

It is clear from Table 4 that the inventive compositions of Examples 22 to 26, which comprise dialdimines of the formula (I) derived from aromatic diamines, compared to the composition of comparative example 27, which comprises a dialdimine derived from an aliphatic diamine, have a significantly longer skin formation time, a higher mechanical strength and a better stability to thermal stress. The inventive compositions have an adequate to very good storage stability and cure without bubbles. Example 24, which comprises a dialdimine of 1,4-phenylenediamine, has a very particularly notable profile of properties.

Examples 29 and 30 and Comparative Example 31

In a screwtop polypropylene beaker, the polymer P-3, the preparation of which is described below, was mixed by means of a centrifugal mixer (SpeedMixer™ DAC 150, FlackTek Inc.; 1 min at 2500 rpm) with the ingredients listed in Table 5 in the proportions by weight specified to give a homogeneous material.

The polymer P-3 was prepared as follows:

590 g of polyoxypropylenediol (Acclaim® 4200 N, Bayer; OH number 28.5 mg KOH/g), 1180 g of polyoxyethylenepolyoxypropylenetriol (Caradol® MD34-02, Shell; OH number 35.0 mg KOH/g) and 230 g of isophorone diisocyanate (IPDI; Vestanat® IPDI, Degussa) were reacted at 80° C. in the presence of 0.01 g of dibutyltin dilaurate to give an NCO-terminated polyurethane polymer with a content of free isocyanate groups of 2.10% by weight.

The ratio between the isocyanate groups and the aldimino groups for all examples is 1.0/0.7.

TABLE 5

Composition of Examples 29 and 30 and of comparative example 31.

| | Example | | |
|---|---|---|---|
| | 29 | 30 | 31 (comparative) |
| Polymer P-3 | 50.0 | 50.0 | 50.0 |
| Dialdimine | A-4, 5.8 | A-5, 6.6 | — |
| Acid catalyst$^a$ | 0.5 | 0.5 | 0.5 |
| Tin catalyst$^b$ | — | — | 0.1 |

$^a$5% by weight of salicylic acid in dioctyl adipate.
$^b$5% by weight of dibutyltin dilaurate in diisodecyl phthalate.

The compositions thus obtained were tested, as described for Example 12, for viscosity, storage stability, skin formation time, bubble formation, mechanical properties and stability to thermal stress. The results of the tests are listed in Table 6.

TABLE 6

Properties of Examples 29 and 30 and of comparative example 31.

| | Example | | |
|---|---|---|---|
| | 29 | 30 | 31 (comparative) |
| Viscosity after 6 h$^a$ | 15.4 | 15.0 | 21.8 |
| Viscosity after 7 d$^a$ | 15.5 | 15.8 | 22.4 |
| $\Delta_{Viscosity}$ (%)$^b$ | 1 | 5 | 3 |

TABLE 6-continued

Properties of Examples 29 and 30 and of comparative example 31.

| | Example | | |
|---|---|---|---|
| | 29 | 30 | 31 (comparative) |
| Skin formation time (min) | 480 | 480 | >720 |
| Bubble formation | none | none | none |
| Tensile strength (MPa)$^c$ | 2.4 | 2.5 | 1.1 |
| | 2.3 | 2.5 | n.m. |
| Elongation at break (%)$^c$ | 400 | 460 | 310 |
| | 400 | 440 | n.m. |
| Modulus of elasticity at 0.5-5% extension (MPa)$^c$ | 1.3 | 1.4 | 1.1 |
| | 1.1 | 1.3 | n.m. |

$^a$in Pa · s, storage at 60° C.
$^b\Delta_{Viscosity}$ = [(viscosity after 7 d/viscosity after 6 h) − 1] × 100%.
$^c$upper figure: testing after curing under standard climatic conditions; lower figure: testing after thermal stress on the cured material (7 d/100° C.).
n.m. = not measurable, since decomposed.

It is clear from Table 6 that the inventive compositions of Examples 29 to 30, which comprise dialdimines of the formula (I) derived from aromatic diamines, compared to the composition of comparative example 31, which does not comprise any dialdimine, have a shorter skin formation time, a higher mechanical strength and better stability to thermal stress. The inventive compositions have very good storage stability and cure without bubbles.

Examples 32 to 36 and Comparative Examples 37 and 38

Elastic Adhesives (For Example for the Adhesive Bonding of Windowpanes)

For each example, the particular constituents according to Table 7 were processed in the parts by weight specified in a vacuum mixer with exclusion of moisture to give a homogeneous paste, which was immediately transferred into an internally coated aluminum cartridge, and the cartridge was sealed air-tight. For comparative example 37, the polymer P-4 and the dialdimine A-8 were heated to 80° C. before mixing, such that the dialdimine A-8 was in liquid form.

The polymer P-4 was prepared as follows:

1300 g of polyoxypropylenediol (Acclaim® 4200 N, Bayer; OH number 28.5 mg KOH/g), 2600 g of polyoxypropylenepolyoxyethylenetriol (Caradol® MD34-02, Shell; OH number 35.0 mg KOH/g), 600 g of 4,4'-methylenediphenyl diisocyanate (MDI; Desmodur® 44 MC L, Bayer) and 500 g of diisodecyl phthalate (DIDP; Palatinol® Z, BASF) were reacted at 80° C. to give an NCO-terminated polyurethane polymer with a content of free isocyanate groups of 2.05% by weight.

The ratio between the isocyanate groups and the aldimino groups is 1.0/0.5 for all examples.

TABLE 7

Composition of the elastic adhesives.

| | Example | | | | | 37 (comp.) | 38 (comp.) |
|---|---|---|---|---|---|---|---|
| | 32 | 33 | 34 | 35 | 36 | | |
| Polymer P-4 | 50.00 | 50.00 | 50.00 | 50.00 | 50.00 | 50.00 | 50.00 |
| Dialdimine | A-1, 4.14 | A-2, 4.17 | A-3, 4.14 | A-4, 4.06 | A-5, 4.62 | A-8, 4.17 | A-9, 4.28 |
| Plasticizer[a] | 9.86 | 9.83 | 9.86 | 9.94 | 9.38 | 9.83 | 9.72 |
| Kaolin[b] | 17.50 | 17.50 | 17.50 | 17.50 | 17.50 | 17.50 | 17.50 |
| Carbon black[b] | 17.50 | 17.50 | 17.50 | 17.50 | 17.50 | 17.50 | 17.50 |
| Desiccant[c] | 0.20 | 0.20 | 0.20 | 0.20 | 0.20 | 0.20 | 0.20 |
| Epoxysilane[d] | 0.30 | 0.30 | 0.30 | 0.30 | 0.30 | 0.30 | 0.30 |
| Acid catalyst[e] | 0.50 | 0.50 | 0.50 | 0.50 | 0.50 | 0.50 | 0.50 |

[a]Diisodecyl phthalate (DIDP; Palatinol ® Z, BASF).
[b]Dried at 130° C.
[c]p-Toluenesulfonyl isocyanate (TI additive, Bayer).
[d]3-Glycidoxypropyl-triethoxysilane (Dynasylan ® GLYEO, Degussa).
[e]5% by weight of salicylic acid in dioctyl adipate.

The elastic adhesives thus obtained were tested for application properties, skin formation time, curing rate, mechanical properties and stability to thermal and hydrolytic stress.

Measures employed for the application properties were creep resistance and threading. To determine creep resistance, the adhesive was applied by means of a cartridge pistol through a triangular nozzle as a horizontal triangular bead with a base diameter of 8 mm and a height (distance of the triangle tip from the base) of 20 mm onto a vertical piece of cardboard. After 5 minutes, the extent to which the tip had dropped, i.e. moved away from the original position in the middle of the triangular bead, was measured. It was assessed as "very good" or "v. good" when the tip was in a completely or nearly unchanged position, and as "good" when the tip was between the middle and the base end. Threading was determined qualitatively by applying a little adhesive by means of a cartridge pistol to a piece of cardboard secured to a wall, pulling the cartridge pistol away from the adhesive applied at the end of the application by pulling it back rapidly, and measuring the length of the thread which remained at the severance point.

A measure employed for the curing rate was the time until the adhesive had cured through. The time until through-curing was examined by applying the adhesive by means of a cartridge pistol through a round tip (opening 10 mm) as a horizontal, free-hanging cone with a length of approx. 50 mm and a thickness in the middle of 30 mm to a piece of cardboard secured to a wall, leaving it under standard climatic conditions over 7 days, then cutting vertically down the middle, and measuring the thickness of the cured adhesive layer with a ruler.

To determine the mechanical properties after the curing, Shore A hardness, tensile strength, elongation at break and modulus of elasticity were measured. Shore A hardness was determined to DIN 53505 on specimens which had been cured under standard climatic conditions over 14 days. Tensile strength, elongation at break and modulus of elasticity were determined on films with a layer thickness of 2 mm, which had been cured under standard climatic conditions over 7 days, in the same way as described in Example 12.

To determine the stability to hydrolytic stress, some of the dumbbells prepared for the measurement of the mechanical properties were stored under hot and humid conditions (70° C./100% relative air humidity) and then under standard climatic conditions for 24 hours, and the mechanical properties were then tested as described.

The remaining properties were tested as described in Example 12.

All adhesives cured completely without bubbles.

The results of the tests are listed in Table 8.

TABLE 8

Properties of the elastic adhesives.

| | Example | | | | | 37 (comp.) | 38 (comp.) |
|---|---|---|---|---|---|---|---|
| | 32 | 33 | 34 | 35 | 36 | | |
| Creep resistance | v. good | v. good | good | v. good | v. good | v. good | good |
| Threading (cm) | 4 | 4 | 1.5 | 1.5 | 1.5 | 1.5 | 2.0 |
| Skin formation time (min) | 245 | 150 | 155 | 105 | 120 | 30 | 35 |
| Through-curing (mm) | 11 | 8 | 12 | 12 | 12 | 9 | 8 |
| Shore A hardness | 70 | 60 | 66 | 76 | 78 | 77 | 78 |
| Tensile strength (MPa)[a] | 8.7 | 8.2 | 8.8 | 8.7 | 9.1 | 8.6 | 8.8 |
| | 11.2 | 8.8 | 11.0 | 11.8 | 12.1 | 11.1 | 10.9 |
| | 10.4 | 8.9 | 10.7 | 11.0 | 11.2 | 10.2 | 10.3 |

TABLE 8-continued

Properties of the elastic adhesives.

| | Example | | | | | | |
|---|---|---|---|---|---|---|---|
| | 32 | 33 | 34 | 35 | 36 | 37 (comp.) | 38 (comp.) |
| Elongation at break (%)[a] | 460 | 520 | 440 | 320 | 380 | 310 | 320 |
| | 320 | 400 | 320 | 250 | 280 | 240 | 310 |
| | 310 | 470 | 330 | 280 | 310 | 260 | 290 |
| Modulus of elasticity at 0.5-5% extension (MPa)[a] | 6.1 | 3.6 | 5.9 | 13.9 | 11.2 | 15.9 | 12.8 |
| | 8.3 | 3.6 | 7.7 | 15.9 | 14.0 | 18.1 | 13.7 |
| | 5.4 | 3.2 | 5.4 | 13.5 | 11.5 | 14.8 | 12.3 |

[a]Upper figure: testing after curing under standard climatic conditions; middle figure: testing after thermal stress on the material cured under standard climatic conditions (7 d/100° C.); lower figure: testing after hydrolytic stress (hot and humid conditions) on the material cured under standard climatic conditions (7 d/70° C., 100% rh).

It is clear from Table 8 that the inventive adhesives of Examples 32 to 36, which comprise aromatic dialdimines of the formula (I), compared to the adhesives of comparative examples 37 and 38, which comprise cycloaliphatic and aliphatic dialdimines, have a significantly longer skin formation time and nonetheless a high curing rate. The inventive adhesives cure without bubbles and possess outstanding mechanical properties.

Examples 39 to 43 and Comparative Example 44

Elastic Sealants (For Example for Joint Sealing)

For each example, the particular constituents according to Table 9 were processed in the parts by weight specified in a vacuum mixer with exclusion of moisture to give a homogeneous paste, which was immediately transferred into an internally coated aluminum cartridge, and the cartridge was sealed air-tight. For comparative example 44, the polymer P-2 and the dialdimine A-8 were heated to 80° C. before the mixing, such that the dialdimine A-8 was in liquid form.

The thickener was prepared as follows:

A vacuum mixer was initially charged with 3000 g of diisodecyl phthalate (DIDP; Palatinol® Z, BASF) and 480 g of 4,4'-methylenediphenyl diisocyanate (MDI; Desmodur® 44 MC L, Bayer) and heated gently. Then 270 g of monobutylamine were slowly added dropwise with vigorous stirring. The paste formed was stirred under reduced pressure with cooling for a further hour.

The ratio between the isocyanate groups and the aldimino groups is 1.0/0.65 for all examples.

TABLE 9

Composition of the elastic sealants.

| | Example | | | | | |
|---|---|---|---|---|---|---|
| | 39 | 40 | 41 | 42 | 43 | 44 (comp.) |
| Polymer P-2 | 24.00 | 24.00 | 24.00 | 24.00 | 24.00 | 24.00 |
| Dialdimine | A-1, 2.77 | A-2, 2.79 | A-3, 2.77 | A-4, 2.71 | A-5, 3.09 | A-8, 2.86 |
| Plasticizer[a] | 0.83 | 0.81 | 0.83 | 0.89 | 0.51 | 1.74 |
| Chalk | 38.00 | 38.00 | 38.00 | 38.00 | 38.00 | 38.00 |
| Thickener | 28.00 | 28.00 | 28.00 | 28.00 | 28.00 | 28.00 |
| Titanium dioxide | 4.50 | 4.50 | 4.50 | 4.50 | 4.50 | 4.50 |
| Desiccant[b] | 0.15 | 0.15 | 0.15 | 0.15 | 0.15 | 0.15 |
| Epoxysilane[c] | 0.25 | 0.25 | 0.25 | 0.25 | 0.25 | 0.25 |
| Acid catalyst[d] | 1.50 | 1.50 | 1.50 | 1.50 | 1.50 | 0.50 |

[a]Diisodecyl phthalate (DIDP; Palatinol® Z, BASF).
[b]Tolylene diisocyanate (TDI; Desmodur® T 80 P, Bayer).
[c]3-Glycidoxypropyltriethoxysilane (Dynasylan® GLYEO, Degussa).
[d]Salicylic acid (5% by weight in dioctyl adipate).

The elastic sealants thus obtained were tested for application properties, skin formation time and mechanical properties after curing, as described for Example 32, except that the curing time of the film for the mechanical testing was 14 days and the extension stress at 100% is reported instead of the modulus of elasticity.

In addition, the sealants were tested qualitatively for tack. This was done by, one day or 3 days after application thereof, pressing the curing Shore A specimens with the thumb and then determining how long the specimen remained adhering on the thumb as the hand was raised. The tack was then assessed as high (specimen remains adhering for more than 3 seconds), moderate (specimen remains adhering for about 3 seconds), low (specimen remains adhering for 1 to 2 seconds) and zero (specimen remains adhering for less than 1 second).

All sealants cured completely without bubbles.

The results of the tests are listed in Table 10.

TABLE 10

Properties of the elastic sealants.

| | Example | | | | | |
|---|---|---|---|---|---|---|
| | 39 | 40 | 41 | 42 | 43 | 44 (comp.) |
| Creep resistance | v. good | v. good | v. good | v. good | v. good | v. good |
| Threading (cm) | 1.0 | 0.5 | 0.8 | 0.8 | 1.5 | 1.5 |
| Skin formation time (min) | 320 | 480 | 265 | 155 | 190 | 40 |
| Shore A hardness | 39 | 29 | 40 | 52 | 38 | 51 |
| Tensile strength (MPa) | 1.8 | 1.1 | 1.6 | 1.7 | 1.5 | 1.7 |
| Elongation at break (%) | 560 | 930 | 440 | 390 | 540 | 150 |
| Extension stress at 100% (MPa) | 1.8 | 0.9 | 1.6 | 1.6 | 1.4 | 1.7 |
| Tack after 1 day | low | high | zero | zero | low | zero |
| Tack after 3 days | zero | low | zero | zero | zero | zero |

It is clear from Table 10 that the inventive sealants of Examples 39 to 43, which comprise aromatic dialdimines of the formula (I), compared to the sealant of comparative example 44, which comprises a cycloaliphatic dialdimine, have a longer skin formation time and a higher elongation at break.

The invention claimed is:

1. An aromatic, room temperature liquid dialdimine of formula (I):

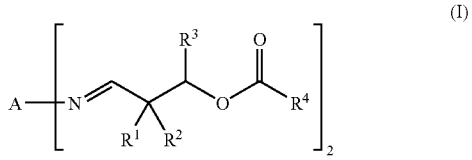

wherein:
A is a radical of a primary aromatic diamine B after removal of two primary amino groups;
the diamine B is selected from the group consisting of 1,2-, 1,3-, and 1,4-phenylenediamine, 2,4- and 2,6-tolylenediamine, 3,4-tolylenediamine, 5-isopropyl-2,4-tolylenediamine, 5-(tert-butyl)-2,4-tolylenediamine, 4,6-dialkyl-1,3-phenylenediamines with alkyl groups, methyl, ethyl, isopropyl or 1-methylpropyl groups, 4,4'-, 2,4'- and 2,2'-diaminodiphenylmethane, 3,3'-dimethyl-4,4'-diaminodiphenylmethane, 3,3'-dichloro-4,4'-diaminodiphenylmethane (MOCA), 3,3'-di-tert-butyl-4,4'-diaminodiphenylmethane, 5,5'-methylenedianthranilic acid, dimethyl 5,5'-methylenedianthranilate, 1,3-propylene bis(4-aminobenzoate), 1,4-butylene bis(4-aminobenzoate), and 1,2-bis(2-aminophenylthio)ethane;
$R^1$ and $R^2$ are each independently either a monovalent hydrocarbon radical having 1 to 12 carbon atoms or together are a divalent hydrocarbon radical which has 4 to 20 carbon atoms and is part of an optionally substituted carbocyclic ring having 5 to 8 carbon atoms;
$R^3$ is a hydrogen atom, an alkyl group, a cycloalkyl group, or an arylalkyl group; and
$R^4$ is either a linear or branched alkyl radical having 6 to 20 carbon atoms, optionally having cyclic moieties and optionally having at least one heteroatom, or $R^4$ is a mono- or polyunsaturated, linear, or branched hydrocarbon radical having 6 to 20 carbon atoms.

2. The aromatic, room temperature liquid dialdimine as claimed in claim 1, wherein $R^1$ and $R^2$ are each a methyl group.

3. The aromatic, room temperature liquid dialdimine as claimed in claim 1, wherein $R^3$ is a hydrogen atom.

4. The aromatic, room temperature liquid dialdimine as claimed in claim 1, wherein $R^4$ is either a linear or branched alkyl radical having 11 to 20 carbon atoms, optionally having cyclic moieties and optionally having at least one heteroatom or $R^4$ is a mono- or polyunsaturated, linear, or branched hydrocarbon radical having 11 to 20 carbon atoms.

5. The aromatic, room temperature liquid dialdimine as claimed in claim 1, wherein the heteroatom optionally present in $R^4$ is oxygen in a form of ether, ester, or aldehyde groups.

6. The aromatic, room temperature liquid dialdimine as claimed in claim 1, wherein $R^4$ is an alkyl radical having 11 carbon atoms.

7. The aromatic, room temperature liquid dialdimine as claimed in claim 1, wherein the diamine B is selected from the group consisting of 1,2-, 1,3- and 1,4-phenylenediamine, 2,4- and 2,6-tolylenediamine, 3,4-tolylenediamine, 4,4'-, 2,4'- and 2,2'-diaminodiphenylmethane, and 3,3'-dichloro-4,4'-diaminodiphenylmethane.

8. The aromatic, room temperature liquid dialdimine as claimed in claim 1, wherein the diamine B is 1,3-phenylenediamine, 1,4-phenylenediamine, 2,4-tolylenediamin; or 4,4'-diaminodiphenylmethane.

9. The aromatic, room temperature liquid dialdimine as claimed in claim 1, wherein the dialdimine of formula (I) at 20° C. has a viscosity of not more than 1000 mPa·s.

10. The aromatic, room temperature liquid dialdimine as claimed in claim 1, wherein the dialdimine of formula (I) is 1,3- and 1,4-bis((2,2-dimethyl-3-lauroyloxypropylidene)amino)benzene, 2,4-bis((2,2-dimethyl-3-lauroyloxypropylidene)amino)toluene, or 4,4'-bis((2,2-dimethyl-3-lauroyloxypropylidene)amino)diphenylmethane.

11. A curable composition comprising:
at least one aromatic, room temperature liquid dialdimine as claimed in claim 1; and
at least one epoxy resin and/or at least one isocyanate.

12. The curable composition as claimed in claim 11, comprising at least one polyisocyanate P.

13. The curable composition as claimed in claim 12, wherein the polyisocyanate P is a polyurethane polymer PUP that is obtainable from a reaction of at least one polyol with at least one polyisocyanate.

14. The curable composition as claimed in claim 12, wherein the polyisocyanate P is a polyisocyanate PI in a form of a monomeric di- or triisocyanate, or of an oligomer of a monomeric diisocyanate.

15. The curable composition as claimed in claim 14, wherein the polyisocyanate PI is an oligomer of 1,6-hexamethylenediisocyanate (HDI), 1-isocyanato-3,3,5-trimethyl-5-isocyanatomethylcyclohexane (=isophorone diisocyanate or IPDI) or 2,4- and 2,6-tolylene diisocyanate, and any mixtures of these isomers (TDI).

16. The curable composition as claimed in claim 12, wherein the polyisocyanate P is a polyisocyanate PI in a form of a room temperature liquid form of 4,4'-, 2,4'- and 2,2'-diphenylmethane diisocyanate and any mixtures of these isomers (MDI), or of a room temperature liquid form of polymeric MDI (PMDI).

17. The curable composition as claimed in claim 12, wherein the polyisocyanate P has aromatic isocyanate groups.

18. The curable composition as claimed in claim 14, wherein the composition further comprises a polyisocyanate P', which is a polyurethane polymer PUP.

19. The curable composition as claimed in claim 12, wherein the polyisocyanate P is present in an amount of 5 to 95% by weight, based on the overall composition.

20. The curable composition as claimed in claim 12, wherein the dialdimine of the formula (I) is present in the composition in such an amount that a ratio between a number of aldimino groups and a number of isocyanate groups is 0.1 to 1.1.

21. The curable composition as claimed in claim 12, further comprising at least a carboxylic acid, and/or a tin compound and/or a bismuth compound as a catalyst.

22. The curable composition as claimed in claim 12, wherein the composition has one component.

23. The curable composition as claimed in claim 12, wherein the composition has two components and consists of a component K1 and a component K2, which are stored separately from one another and are mixed with one another before the application.

24. The curable composition as claimed in claim 23, wherein:
the polyisocyanate P and the dialdimine of the formula (I) are part of component K1, and
component K2 comprises compounds reactive toward isocyanate groups.

25. The curable composition as claimed in claim 23, wherein:
the polyisocyanate P is part of component K1, and
component K2 comprises the dialdimine of the formula (I) and compounds reactive toward isocyanate groups.

26. The curable composition as claimed in claim 25, wherein component K2 comprises at least one dialdimine of the formula (I) and water.

27. A cured composition which is obtained by a reaction of a composition as claimed in claim 12 with water.

28. A cured composition that is obtained by mixing the two components K1 and K2 of a composition as claimed in claim 23, optionally followed by a reaction with water.

29. An adhesive, sealant, potting composition, coating, floor covering, paint, lacquer, primer or foam comprising the curable composition as claimed in claim 11.

30. A method of bonding window panes in a motor vehicle comprising applying the adhesive of claim 29 to a window pane.

31. A process for adhesive bonding a substrate S1 to a substrate S2, the process comprising:
i) applying the curable composition to a substrate S1;
ii) contacting the applied composition with a substrate S2 within an open time of the composition;
or
i') applying a curable composition as claimed in claim 11 to a substrate S1 and to a substrate S2;
ii') contacting the applied compositions with one another within an open time of the composition.

32. An adhesive bonded article which is obtained by the process as claimed in claim 31.

33. The article as claimed in claim 32, wherein the article is a built structure, or an industrial good or a consumer good, a domestic appliance, or a mode of transport, or an installable component of a mode of transport, or an article in the furniture, textile or packaging industry.

* * * * *